United States Patent
Welzel

(10) Patent No.: US 10,799,526 B2
(45) Date of Patent: Oct. 13, 2020

(54) MEDIUM MOLECULAR WEIGHT HEPARIN

(71) Applicant: Fytagoras B.V., Leiden (NL)

(72) Inventor: Dieter Welzel, Nuremberg (DE)

(73) Assignee: Fytagoras B.V., Leiden (NL)

( * ) Notice: Subject to any disclaimer, the term of this patent is extended or adjusted under 35 U.S.C. 154(b) by 0 days.

(21) Appl. No.: 16/475,542

(22) PCT Filed: Jan. 9, 2018

(86) PCT No.: PCT/EP2018/050448
§ 371 (c)(1),
(2) Date: Jul. 2, 2019

(87) PCT Pub. No.: WO2018/130519
PCT Pub. Date: Jul. 19, 2018

(65) Prior Publication Data
US 2019/0350966 A1    Nov. 21, 2019

(30) Foreign Application Priority Data
Jan. 11, 2017  (EP) .................................... 17151025

(51) Int. Cl.
*A61K 31/727* (2006.01)
*A61P 7/02* (2006.01)

(52) U.S. Cl.
CPC .............. *A61K 31/727* (2013.01); *A61P 7/02* (2018.01)

(58) Field of Classification Search
None
See application file for complete search history.

(56) References Cited

U.S. PATENT DOCUMENTS

2008/0119438 A1    5/2008  Weitz et al.

FOREIGN PATENT DOCUMENTS

EP    1 252 194 B1    10/2004
WO    01/51525 A1    7/2007

OTHER PUBLICATIONS

Guyatt, et al., Antithrombotic Therapy and Prevention of Thrombosis, 9th Ed: American College of Chest Physicians Evidence-Based Clinical Practice Guidelines, Chest/141/2/Feb. 2012 Supplement.
Lyman et al., American Society of Clinical Oncology Guideline: Recommendations for Venous Thromboembolism Prophylaxis and Treatment in Patients with Cancer, 2007 by American Society of Clinical Oncology.
Leonardi et al., A Systematic Review of Deep Venous Thrombosis Prophylaxis in Cancer Patients Implications for Improving Quality, M.J Leonardi et al. Annals of Surgical Oncology 14 (2) 1929-36 (2007).
R. Al Dieri et al., The Inhibition of Blood Coagulation by Heparins of Different Molecular Weight is Caused by a common Functional Motif—the C-Domain, Journal of Thrombosis and Haemostatis, 1:907-914.
Ji Weitz et al., Clot-bound Thrombin is Protected From Inhibition by Heparin-antithrombin III but Is Susceptible to Inactivation by Antithrombin III-Independent Inhibitors, The Journal of Clinical Investigation, 1990;86(2): 385-391. https://doi.org/10.1172/JCI114723.
Becker et al., Exosites 1 and 2 are Essential for Protection of Fibrin-bound Thrombin from Heparin-catalyzed Inhibition by Antithrombin and Heparin Cofactor II, The Journal of Biological Chemistry, The American Society for Biochemistry and Molecular Biology, Inc., vol. 274, No. 10, Issue of Mar. 5, pp. 6226-6233, 1999.
Kakkar, et al., Extrinsic-pathway activation in cancer with high factor VIIa and tissue factor, Lance, Oct. 14, 1995;346 (8981):1004-5.
Shapiro et al., Making contact with microparticles; Journal of Thrombosis and Haemostatis, 10:1352-1354.
Morel et al., Procagulant microparticles: disrupting the vascular homeostasis equation?; Arterioscler Thromb Vasc Biol. Dec. 2006;26(12):2594-604. Epub Sep. 21, 2006.
Furie, et al., Mechanisms of Thrombus Formation; The New England Journal of Medicine, 2008:359:938-49;www.nejm.org, Aug. 28, 2008.
Abildgaard et al, Heparin Requires both Antithrombin and Extrinsic Pathway Inhibitor for Its Anticoagulant Effect in Human Blood, Haemostasis 1991;21:254-257.
P.A. Ockelford, et al., Comparison of the In Vivo Hemorrhagic and Antithrombotic Effects of a Low Antithrombin-III Affinity Heparin Fraction; Thrombosis Research 27;679-690,1982.
Johansen et al.,Tinzaparin and other low-molecular weight heparins: what is the evidence for differential dependence on renal clearance?; Johansen and Balchen Experimental Hematology & Oncology 2013,2:21; http://www.ehoonline.org/content/2/1/21.
Schmid et al., Low-molecular-weight heparin in patients with renal insufficiency.; Swiss Med Wkly. Aug. 8, 2009;139(31-32):438-52. doi:smw-11284.
Launay-Vacher et al., Prevalence of Renal Insufficiency in cancer patients and implications for anticancer drug management: the renal insufficiency and anticancer medications (IRMA) study.;Cancer. Sep. 15, 2007;110(6):1376-84.
Carrier et al.,Clinical challenges in patients with cancer-associated thrombosis: Canadian expert consensus recommendations; Curr Oncol. Feb. 2015; 22(1):49-59.

(Continued)

*Primary Examiner* — Layla D Berry
(74) *Attorney, Agent, or Firm* — Seth L. Hudson; Clements Bernard Walker

(57) ABSTRACT

The present invention concerns medium molecular weight heparin (MMWH 10.5 kD) for prevention and treatment of venous thromboembolism in malignant disease.

1 Claim, 18 Drawing Sheets

(56) References Cited

OTHER PUBLICATIONS

Harenberg; Past, present, and future perspectives of heparins in clinical settings and the role of impaired renal function; International Journal of Cardiology 212S1 (2016) S10-S13; www.elsevier.com/locate/ijcard.
Leyvraz et al., Adjusted Versus Fixed-Dose Subcutaneous Heparin in the Prevention of Deep-Vein Thrombosis After Total Hip Replacement; The New England Journal of Medicine; Oct. 20, 1983.
Cohen et al., Epidemiology of first and recurrent venous thromboembolism in patients with active cancer; Thrombosis and Haemostasis Jan. 2017, 717 p. 57 and p. 64.
Lindahl et al., Release of Extrinsic Pathway Inhibitor After Heparin Injection:Increased Response in Cancer Patients; Thrombosis Research vol. 59, No. 3; 651-656,1990.
Schinzel et al., Einsatz von niedermolekularen Heparinen bei Niereninsuffizienz; Vascular Care Jan. 2007 vol. 12, pp. 18-31.
Kasthuri et al., Role of tissue factor in cancer.; Journal of Clinical Onocology, Oct. 10, 2009;27(29):pp. 4834-4838.
Hogg et al.,Heparin Promotes the Binding of Thrombin to Fibrin Polymer; The Journal of Biological Chemistry; vol. 265, No. 1, Issue of Jan. 5, pp. 241-247, 1990.
Ma et al., Molecular weight dependent tissue factor pathway inhibitor release by heparin and heparn oligosaccharides; Thromb Res. 2007;119(5):653-61. Epub Jul. 7, 2006.
Alban et al., Pharmacokinetic and Pharmacodynamic Characterization of a Medium-Molecular-Weight Heparin in Comparison with UFH and LMWH; Seminars in Thrombosis and Hemostasis;vol. 28, No. 4, Aug. 2002 p. 369-377.
Bell et al., Prevention of venous thromboembolism in the Enhanced Recovery After Surgery (ERAS) setting: an avidence-based review; Canadian Anesthesiologists (2015) vol. 62 No. 2, Nov. 13, 2014; pp. 194-202.
Qureshi et al., Venous Thromboembolism in Cancer: An Update of Treatment and Prevention in the Era of Newer Anticoagulants; Frontiers in Cardiovascular Medicine; Jul. 28, 2016; vol. 3, Article 24 pp. 1-11.
Lim et al.; Safety of anticoagulation in the treatment of venous thromboembolism in patients with haematological malignancies and thrombocytopenia: Report of 5 cases and literature review; Clinical Reviews in Oncology/Hematology; vol. 105, Jun. 26, 2016; pp. 92-99.
Van Es et al., Cancer-associated unsuspected pulmonary embolism; Thrombosis Research vol. 133 S2, May 2014, S172-S178; www.elsevier.com/locate/thomres.
Scotte et al.; Thrombosis, cancer and renal insufficiency: low molecular weight heparin at the crossroads; Support Care Cancer Sep. 9, 2012, vol. 20, No. 12; pp. 3033-3042.
Leizorovicz et al., Safety profile of tinzaparin versus subcutaneous unfractionated heparin in elderly patients with impaired renal function treated for acute deep vein thrombosis:the Innohep in Renal Insufficiency Study (IRIS); Thomb Res. Jul. 2011;128(1):27-34.
Professor Dr. Med. J. Harenberg, Universitatsklinikum Mannheim; D-68167 Mannheim; May 15, 2001.
Dahm et al., Low levels of tissue factor pathway inhibitor (TFPI) increase the risk of venous thrombosis; Blood. Jun. 1, 2003;101(11):4387-92. EpubJan. 30, 2003.
Duering et al., Total tissue factor pathway inhibitor is an independent risk factor for symptomatic paediatric venous thromboembolism and stroke; Thromb Haemost 2004; 92(04):707-712.
Langer et al., Crosstalk between cancer and haemostasis Implications for cancer biology and cancer-associated thrombosis with focus on tissue factor;www.haemostaseologie-online.com on Jul. 18, 2016.
Himber et al., Dissociation of antithrombotic effect and bleeding time prolongation in rabbits by inhibiting tissue factor function; Thromb Haemost, Sep. 1997;78(3):1142-9.
Ragni et al., Endogenous tissue factor pathway inhibitor modulates thrombus formation in an in vivo model of rabbit carotid artery stenosis and endothelial injury; Circulation. Jul. 4, 2000; 102(1):113-7.
Golino et al., Involvement of tissue factor pathway inhibitor in the coronary circulation of patients with acute coronary syndromes. Circulation.Dec. 9, 2003;108(23):2864-9; Epub Dec. 1, 2003.
Brodin et al., Regulation of thrombin generation by TFPI in plasma without and with heparin. Transl Res. Mar. 2009;153 (3); 124-31. doi: 10.1016/j.trsl.2008.12.004. Epub Jan. 7, 2009.
Hirsh; Low Molecular Weight Heparins, Taschenbuch—2007.
Carter; The relationship between the hemorrhagic and antithrombotic properties of low molecular weight heparin in rabbits; Blood. Jun. 1982;59(6):1239-45.
Berggvist et al., The effect of heparin fragments of different molecular weights on experimental thrombosis and haemostasis; Thromb Res. Jun. 15, 1985;38(6):589-601.
Matthiasson et al., The Haemorrhagic Effect of Low Molecular Weight Heparins, Dermatan Suphate and Hirudin; Haemostasis 1995; 25:203-211.
Welzel et al., Prophylaxis of venous thromboembolism: low molecular weight heparin compared to the selective anticoagulants rivaroxaban, dabigatran and fondaparinux; Int Angiol. Jun. 2011; 30(3): 199-211.
Zwicker et al., Tumor-derived tissue factor-bearing microparticles are associated with venous thromboembolic events in malignancy; Clin Cancer Res. Nov. 15, 2009; 15(22):6830-40.
Lim et al., Meta-analysis: low-molecular-weight heparin and bleeding in patients with severe renal insufficiency; Ann Intern Med. May 2, 2006; 144(9):673-84.

MEDIUM MOLECULAR WEIGHT HEPARIN

FIELD OF THE INVENTION

The present invention concerns medium molecular weight heparin (MMWH 10.5 kD) for prevention and treatment of venous thromboembolism in malignant disease.

BACKGROUND OF THE INVENTION

Malignancies and major surgery related are associated with extraordinary high risks of venous thromboembolism (VTE) and bleeding complications that defy the established therapeutic measures.

VTE is a frequent complication of the primary illness in hospital-patients and those having undergone for example total hip replacement, abdominal or pelvic operation for cancer. The majority of pulmonary emboli originating in deep vein thrombosis" (DVT) occur without premonitory signs.

From the prior art it is known to prevent such type of complications by applying an effective method of prophylaxis with unfractionated heparin (UFH) or low molecular weight heparins (LMWHs). The latter are dealt with as a class in the international guidelines—the leading one being the "Antithrombotic Therapy and Prevention of Thrombosis" ($9^{th}$ Ed. ACCP Guidelines 2012)—because LMWHs do not differ in terms of effectiveness and bleeding complications associated, i.e., in their benefit-risk ratio.

With respect to the aforementioned heparin agents known from the prior art, there seems no room left for any procedural improvements. UFH and LMWH alike are completely exploited not allowing for stepping up the fixed dosage-regimens without a significant increase of major bleeding-events. A look at the ACCP Guidelines evidences the efforts spent in order to find the right prophylactic approach by balancing the risk of VTE on the one hand and that of bleeding on the other.

The risk of perioperative VTE can be quantified in terms of the Roger Score or—more customary—the Caprini Score. As a typical example in cancer disease, a 60 to 74 years old patient, undergoing major surgery (more than 45 min.) because of some malignancy, confined to bed for more than 72 hours, winds up with a Caprini Score of 8 which is indicative for a very high risk of VTE.

It is of interest here that in high risk categories of VTE (Caprini Score of 5 and above) mechanical prophylaxis, preferably with IPC (intermittent pneumatic compression of the calf), is recommended, alone or in conjunction with LMWH or low-dose UFH. In case of high-risk bleeding, exclusive or primary preference is given to mechanical prevention, which is devoid of side effects but marginally effective only and burdensome for the patients and the staff.

The American Society of Clinical Oncology Guideline (2007) and M. J. Leonardi et al. (Annals of Surgical Oncology 2007. Vol. 14, 1929-36) furnish comprehensive information on the incidences of VTE and the pertinent bleeding complications in malignant diseases.

In elderly patients the risk of VTE is even more pronounced than in younger ones resulting in a 3 times higher incidence of fatal pulmonary embolism (3.7% vs 1.1%), and the danger of fatal bleeding is twice as frequent. Even high-dose heparin prophylaxis, e.g., with Enoxaparin® 4000 U, or Dalteparin® 5000 U, does not suppress the incidence of DVT below 8%.

The recurrence of VTE during long-term treatment with LMWH or vitamin K antagonists also brings up significant problems.

Heparins of natural origin, UFH and LMWH alike, act first and foremost via their antithrombin-(antFIIa) effect. That is the state of the art in heparinology based upon the pioneering research of H. C. Hemker (Maastricht) and his school (R. A. Dieri et al. and H. C. Hemker, J Thrombosis and Haemostasis 2002, 1, 907-914).

VTE in malignancies essentially refers to clinically manifest processes, i.e., to symptomatic thromboembolism arising from the asymptomatic stage. J. Weitz et al. (J Clin Invest 1990, 86, 385-392) and D. Becker et al. (3 Biol Chem 1999, 274, p. 6226-6233) explain how, to become symptomatic, venous thrombi are first subject to growth and extension by accretion of fibrin. Against this background, a special therapeutic problem emerges: Fibrin restricts the anticoagulatory action of unfractionated heparin (UFH). The long-chain molecules of the latter are bridged to thrombin, whereby the critical binding site on the thrombin as specifically necessary for its neutralisation by the antithrombin III-heparin complex is occupied.

Against this background, the question arises why the well-established LMWHs cannot be used as substitutes for UFH in this respect. It is because of their molecular weight-dependent, genuinely weak anti-thrombin activity, that they are insufficient in order to counteract advancing thrombosis better than UFH. The required doses would be too high as to be well tolerable, i.e., without an excessive exposure to bleeding-complications. In this way, the advantage of LMWH's short heparin chains cannot overcome the relative deficiency in antithrombin activity.

As demonstrated by A. K. Kakkar (LANCET 1995, 346, 1004-1005) in a key-investigation, tissue factor (TF) and factor VIIa are present with higher plasma-concentrations in cancer patients than in control cases with statistical significance, which indicates a pathological activation of the extrinsic pathway of coagulation. The resulting excess thrombin-generation is characterized by the elevation of the thrombin/antithrombin III-complex (TAT), in which the enzyme is covalently bound and irreversibly inhibited (FIG. 15). S. Shapiro et al. (I Thromb Haemost 2012, 10, 1352-54) and O. Morel et al. (Thromb Vasc Biol 2006, 26, 2594-604) explain how tumor cells release TF-positive microparticles into the circulation that can trigger VTE and significantly contribute to thrombus-extension (FIG. 16). It is the TF-driven stimulation of the coagulation system in cancer that suggests specified therapeutic interventions.

As pointed out by B. Furie et al. (New England Journal of Medicine 2008, 359, 938-949), "inhibition of tissue factor or prevention of microparticle accumulation might provide prophylactic treatment against cancer-associated thrombosis." That prominent statement directs the attention to the role of the "tissue factor pathway inhibitor" (TFPI). TFPI is a plasma protease inhibitor that regulates the TF-induced pathway of coagulation by inactivating both the TFN/VIIa-complex and FXa. Its structure permits the inhibitor to exert its dual control.

Circulating plasma TFPI is partly bound to lipoproteins, and only the carrier-free inhibitor has an influence upon the coagulation-system.

TFPI exerts its anticoagulatory impact by a feedback inhibitory mechanism involving first the binding of factor Xa and then the formation of a quaternary inhibition complex including TF/VIIa, FXa, and TFPI.

Abildgaard et al. (Haemostasis 1991, 21, 254-57) describe how TFPI contributes significantly (about one third) to the anticoagulatory potential of heparin.

To develop antithrombotics the sparing of hemostasis to a large extent is of overriding significance. Given this developmental principle it need be realized that within the various classes of antithrombotic drugs (heparins, vitamin-K-antagonists, factor Xa- and thrombin-inhibitors) there are no proven differences in terms of their benefit-risk-ratio (therapeutic window).

So-called "low affinity molecules", which are abundantly found in natural heparins, induce significant haemorrhage without exerting any anticoagulatory/antithrombotic effect. LMWHs contain especially plenty of "low affinity material" (LAM).

By a series of sophisticated experiments, P. A Ockelford et al. (Thrombosis Research 1982, 27, p. 679-90) quantified the differential impact of HAM and LAM in regard to both their anti-thrombotic and bleeding-inducing potential (FIG. 17). According to the results the inhibition of thrombogenesis is entirely due to the so-called "high affinity material" (HAM) whereas half of the heparin-related excess blood loss proves to be due to LAM.

Heparin consists of unbranched polysaccharide chains composed of alternating uromate and hexosamin-saccharides. In order to neutralize the activated clotting factors heparin first must form a stoichiometric covalent inhibitor complex with antithrombin III in plasma which requires a specific pentasaccharide (PS) sequence in the given heparin chain. Those chains exhibiting the critical PS sequence are the only ones exerting any anticoagulatory effect and constitute the so-called high-affinity material (HAM).

The distribution of the PS sequence within in the mixture of natural heparin chains is random, i.e., the longer the given chain, the higher the probability that a PS sequence is present.

That is why LMWHs contain only a minor fraction of HAM, the rest belonging to the LAM species. By way of example, the LMWH model substance enoxaparin just involves 14% of its molecules belonging to HAM.

Johansen et al. (Experimental Hematology Oncology 2013, 2, 21) and Schmid et al. (Swiss Med WKLY 2009, 139, 438-452) describe how LMWHs are partially metabolized by depolymerisation and/or desulfatation and excreted via the kidneys. The elimination is reduced in subjects with impaired renal function. The associated bioaccumulation of LMWHs is of particular concern in populations with a high prevalence of renal impairment, such as the elderly and patients with cancer.

The results of the Renal Insufficiency and Cancer Medication (IRMA) Study by V. Launay-Vacher et. al. (Cancer 2007, 15, 110 (6), 1376-84), which included 4684 patients and 15 centres, are most instructive. Nearly 60% of the study group presented with renal insufficiency according to the Working Group of the National Kidney Foundation, 20% of the population exhibiting "moderate" to "severe" renal "disease".

VTE, bleeding events and renal disease are significantly interrelated. According to the recent Canadian Expert Consensus Recommendations (Current Oncology 2015, 22, p. 49-59) LMWHs should be avoided in patients with progressed renal disease unless they are monitored using antifactor Xa levels.

The problem, however, is that little evidence has been developed to show this practice improves outcomes when used to guide LMWH-dosing, so the statement of the Canadian experts.

Regarding the LMWH agents certoparin, reviparin, nadroparin, and enoxaparin, clear-cut precautionary measures or contraindications are given, if the creatinin-clearance, a central parameter of renal function, falls below 30 ml/min.

In the framework of IRMA (see above) more than 50% of the more than 7000 anti-cancer drug prescriptions required dose adjustments for renal impairment. That is exactly what is stipulated for the standard and by far mostly used LMWH enoxaparin: a 25% dose-reduction in prophylaxis and a 50% one in VTE-therapy. Nevertheless an increased major bleeding risk in patients with kidney dysfunction receiving enoxaparin was found in a special metanalysis by J. Harenberg et al. (Int. J. Cardiology 2016, 212, 510-513). Major bleeding occurred twice as frequent (5% vs. 2.4%, p=0.013) than in association with a creatinin-clearance of more than 30 ml/min.

Heparins in general are subject to substantial fluctuations in bioavailability as reflected by high standard deviations of blood levels. The control of the activated partial thromboplastin time (APTT) is a laboratory guide to a more accurate and targeted dose-strategy. According to the Canadian Expert Consensus 2015, extensive practical experience suggests that unfractionated heparin inventoried by the APTT is a practical approach for therapeutic anticoagulation in patients with renal insuffiency which per se is laden with bleeding-problems.

Leyvraz et al. (N Engl 3 Med 1983, 309, 954-58) argue that conventional prophylaxis with UFH could be substantially improved by monitoring the doses and adjusting them according to the APTT. In this way the incidence of venous thromboembolism could be reduced by 66% as compared to the standard (low dose) heparin-regime without allowances to bleeding events.

So the extraordinary medical need to improve upon prevention and management of VTE as reflected by the ACCP-Guidelines and substantiated by the medical societies is beyond doubt.

Alexander T. Cohen; Anja Katholing; Stepahn Riebrock; Luke Bamber; Carlos Martinez; Thrombosis and Haemostasis January/2017, 57 to 64 discloses that population studies on the incidence of nevous thromboembolism (VTE) in patients with active cancer are limited. An observational cohort study was undertaken to estimate the incidence of first and recurrent VTE. The source population consisted of all patients in the UC Clinical Practice Research Datalink, with additional information on hospitalization and cause of death, between 2001 and 2011. A cancer-related clinical diagnosis of therapy within the 90 day before or after a VTE constituted an active-cancer-associated VTE. Incidence rates of first VTE among patients with active cancer and incidence rated of recurrent VTE during the 10-year observational period after a first VTE event were estimated. Incidence rates of all cause mortality and age- and gender-specific mortality were also calculated. There were 6,592 active-cancer-associated VTEs with a total of 112,738 cancer-associated person-years of observation. The incidence rate of first VTE in patients with active cancer was 5.8 (95% confidence interval 5.7-6.0) per 100 person-years. A first VTE recurrence was observed in 591 patients. The overall incidence rate for recurrence was 9.6 (95% confidence interval 8.8-10.4) per person-years, with a peak at 22.1 in the first six months. Recurrence rates were similar after initial pulmonary embolism and after initial deep-vein thrombosis. The mortality risk after VTE was considerable, with 64.5% mortality after one year and 88.1% after 10 years. VTE in patients with active cancer is common and associated with high recurrence and mortality rates. Efforts are needed to prevent VTE and reduce recurrence, especially in the first year after VTE diagnosis.

Said article shows the enormous still existing need to prohibit VTE for patients suffering from cancer malignant disease.

BRIEF SUMMARY OF THE INVENTION

It is thus the problem of the present invention to overcome the shortcomings of the state-of-the-art treatment of venous thromboembolism in malignant diseases. Particularly it is the aim of the present invention to provide a drug for treatment of VTE that has a unique benefit-risk-ratio, i.e., an exceptional anti-thrombin/anti-thrombotic activity combined with a reduced bleeding intensity as compared to LMWH. Moreover, it should comply with certain aspects of activity that could translate into an even heightened benefit risk-ratio in cancer thus supporting the specificity of the indication. Another aim of the present invention is to provide said drug for the treatment of cancer, particularly cancer complicated with renal disease. Such drug should show promise to overcome the insufficient antithrombotic response to LMWH and UFH, and be appropriate in improving the tolerance of anticoagulation.

In a first aspect of the invention the problem is solved by a medium molecular weight heparin (MMWH) for use in the treatment of venous thromboemoblism in malignant disease.

The MMWH used according to the present invention is a heparin with an average molecular weight (MW) between that of UFH and LMWH and with a particularly narrow MW distribution.

In this way, said heparin contains neither a sizable amount of molecules with MW greater than 15 kD, as are characteristic of UFH, nor a sizable amount of short-chain molecules (BCLM) exhibiting a Xa activity only. It thus combines the favourable bioavailability of LMWH with the high specific anticoagulant activity of UFH.

The preparation of said medium molecular weight heparin is described in EP 1 252 194 B1.

Due to its unique narrow-cut molecular profile, the inventive MMWH combines a high antithrombin-activity in men (on a molar and on a gravimetric basis) with a truncated potential of haemorrhage.

Surprisingly, the haemostaseological armamentarium manifests itself in an unparalleled, experimentally proven antithrombotic effectiveness concurring with a significantly reduced bleeding activity.

The primary pharmacological impact factors are enhanced by auxiliary ones that include specific and important influences upon VTE in malignant disease. In particular these properties concern first the uncurtailed activity towards clot-bound thrombin as stimulating thrombus-growth which proves less susceptible to UFH and LMWH alike, secondly the unmatched release of tissue factor pathway inhibitor (TFPI) as directly interfering with tumor-driven thrombogenesis, thirdly the substantial exclusion of the so-called low-affinity material (LAM) from the molecular spectrum comprising those molecules that do not contribute to the anti-thrombotic potential, but nevertheless induce bleeding. In the fourth place, it is the absence of bioaccumulation in renal failure as a regular co-morbid accompaniment in malignancies implying an even more accentuated risk of both VTE and bleeding complications.

In case of MMWH there are no restrictions or contraindications to observe as in contrast to LMWH and the benchmark product enoxaparin especially.

The MMWH's differential disease-specific suitability is rounded off by the opportunity to adapt the doses applied according to the activated partial thromboplastin time (APTT), a laboratory method lending itself to some further heightening of effectiveness without allowances to tolerance.

In a preferred embodiment of the invention, the medium molecular weight heparin has an average molecular weight of more than 9 kD and less than 12 kD. More preferably the average molecular weight of the MMWH is 10 kD to less than 11.5 kD. Most preferably the average molecular weight of the MMWH is 10.5 kD.

In what follows, the benefits of the inventive MMWH for use in the treatment of venous thromboembolism in malignant diseases are described more particularly. The description is exemplary and not meant to limit the scope of the invention.

BRIEF DESCRIPTION OF THE DRAWINGS

The present invention is illustrated and described herein with reference to the drawing, in which like reference numbers denote like method steps and/or system components, respectively, and in which.

DETAILED DESCRIPTION OF THE INVENTION

The overall endpoint-benefit of MMWH's haemostaseological characteristics is based on its unsurpassed antithrombotic activity which is at least partially decoupled from the inherent tendency towards bleeding. That optimized benefit-risk profile surprisingly opens up the unprecedented access to personalized VTE prevention in malignant disease with the dosage-regimen being applied depending on the prevailing risk of either thrombosis or bleeding.

Surprisingly, MMWH is therefore more efficient and also safer than other heparins, especially because substantially lower doses (on a weight and a molar basis) are sufficient to bring about effects comparable to those of UFH and LMWH.

Figure 1A:
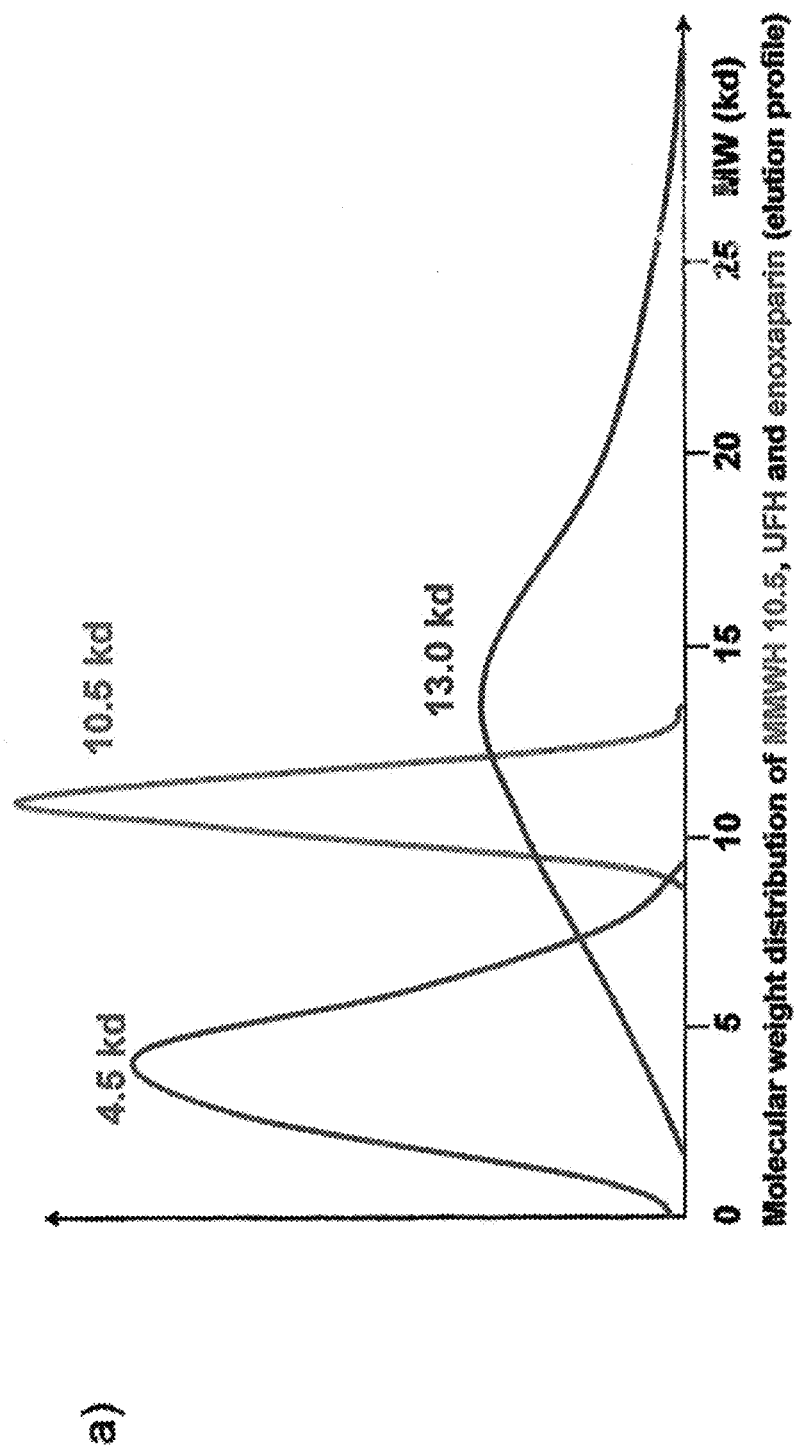
FIG. 1a shows the molecular weight distribution of an exemplary embodiment of the MMWH, UFH and the LMWH enoxaparin. The fraction with an average molecular weight of 4.5 kD corresponds to enoxaparin, the fraction with an average molecular weight of 10.5 kD corresponds to MMWH and the fraction with an average molecular weight of 13.0 kD corresponds to UFH.
Figure 1B:
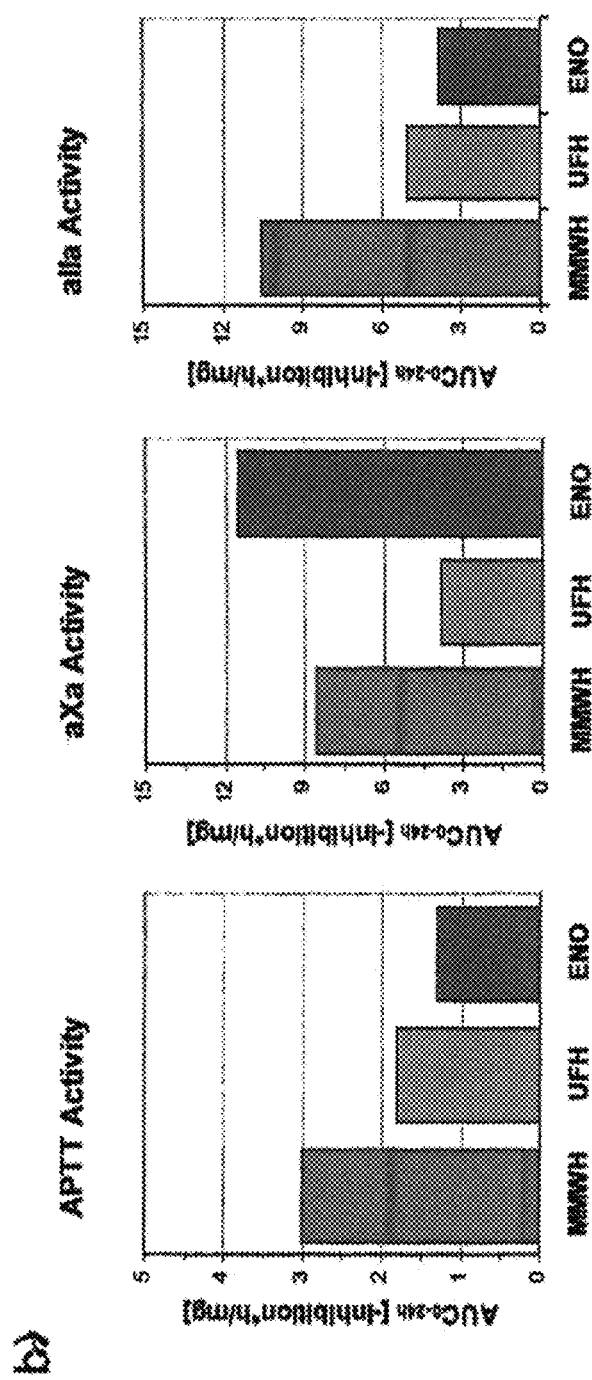
FIG. 1b shows the 24 hour integrated anticoagulatory activities in men (AUC 0-24 values, based upon the per-mg doses administered) in MMWH, UFH and enoxaparin (ENO).
Figure 2:
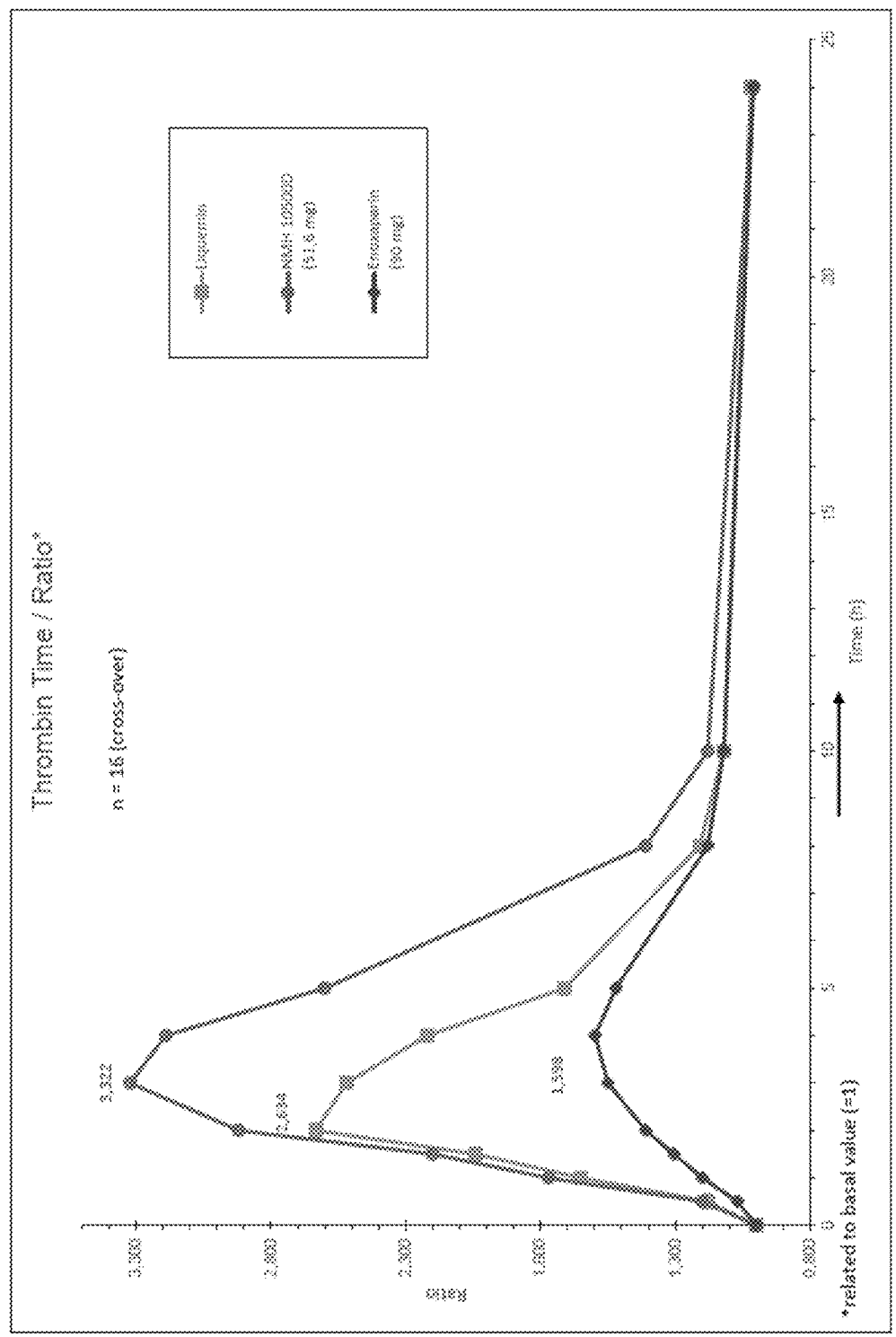
FIG. 2 shows the thrombin time of various heparins as a ratio related to basal value (=1) for a study group of n=16 (cross-over).
Figure 3:
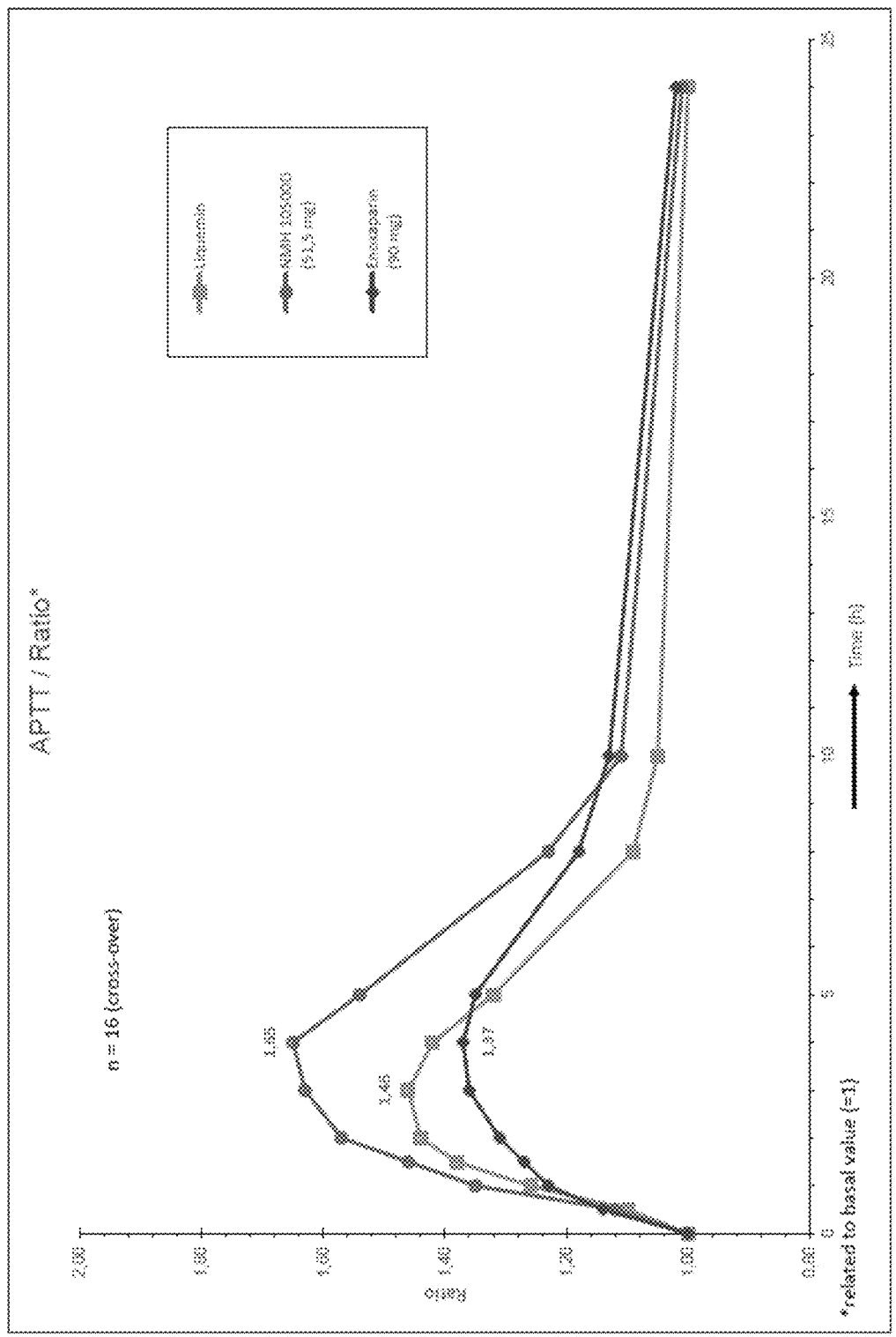
FIG. 3 shows the activated partial thromboplastin time (APTT) of various heparins as a ratio related to basal value (=1) for a study group of n=16 (cross-over).
Figure 4:
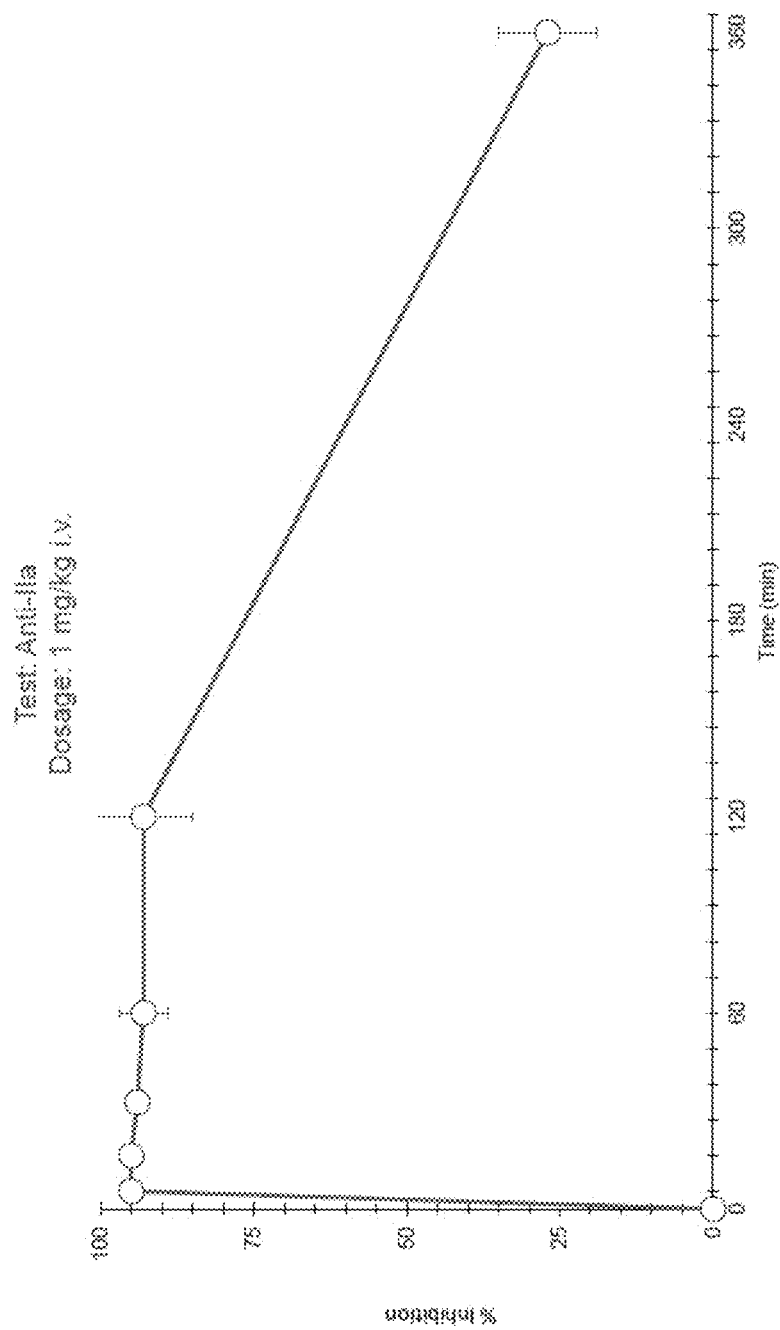
FIG. 4 shows the anti-Ha activity of the medium molecular weight heparin in primates after intravenous administration of 1 mg/kg.
Figure 5:
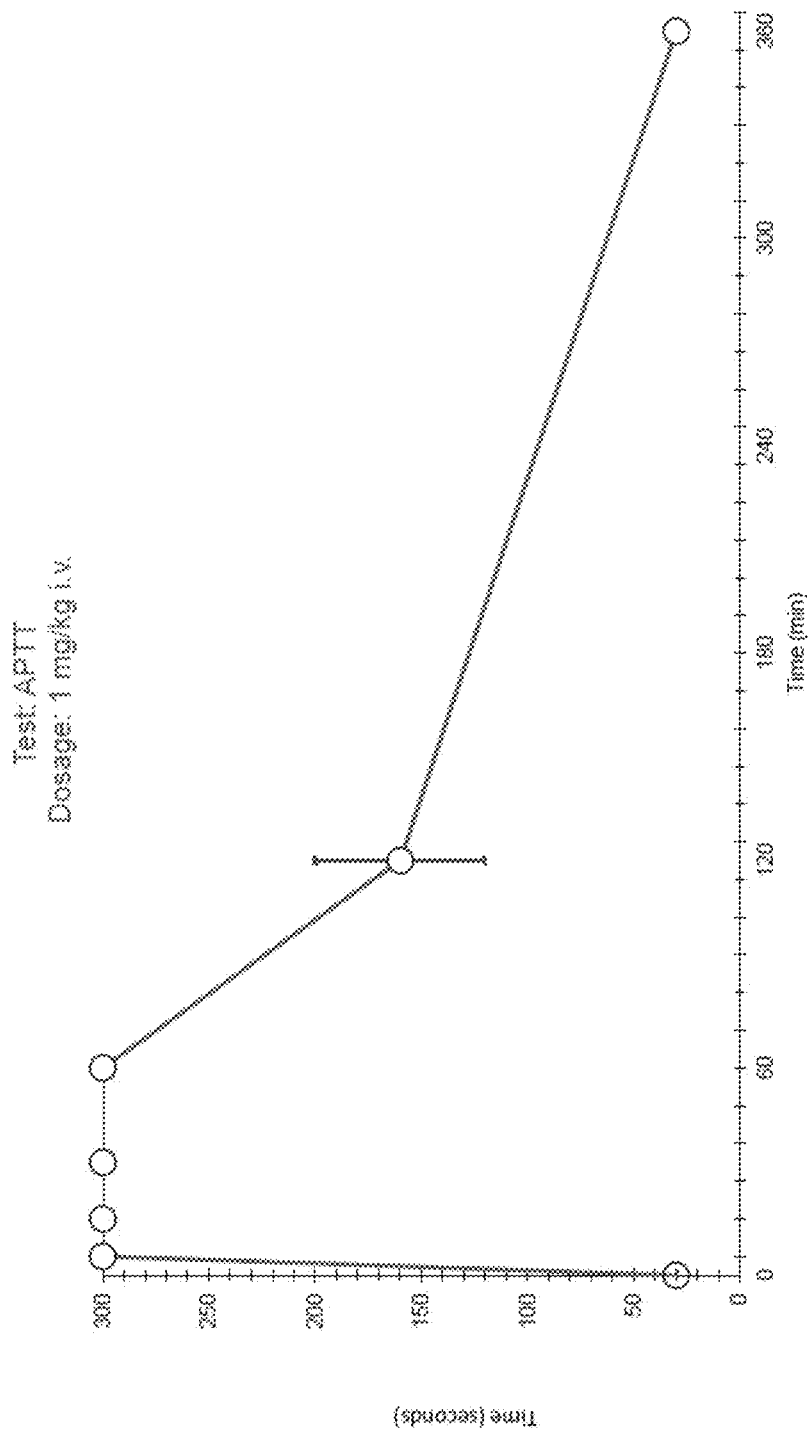
FIG. 5 shows the APTT activity of the inventive medium molecular weight heparin in primates after intravenous administration of 1 mg/kg.

As a matter of fact, the 24 hour integrated antithrombin antF/IIa effect of MMWH in men amounts to 260% and 200% as compared to LMWH (enoxaparin) and UFH respectively (Table 1, FIG. 1 b). The so-called thrombin time as the most specific antFIIa-test evidences the unique superiority of MMWH, the same holding true for the activated partial thromboplastin time (APTT), which measures how endogeneous thrombin is influenced by heparins (FIG. 2, 3). In rounding off the extraordinary anticoagulatory properties of MMWH complementary experiments were performed in primates which underscore the unique maximized antFIIa potential of the product (FIG. 4, 5).

TABLE 1

In vitro activities of the three heparins

|  | aXa U/mg | aIIa U/mg | aXa/aIIa ratio | aIIa/aXa ratio |
|---|---|---|---|---|
| MMWH 10.5 | 174.9[1] | 170.0[1] | 1.03 | 0.97 |
| UFH | 159.0[2] | 159.0[2] | 1.00 | 1.00 |
| Enoxaparin | 199.9[2] | 26.3[2] | 3.80 | 0.26 |

[1]measured by the 1st int. standard for LMWH
[2]measured by the 4th int. standard for UFH The primary task consists in elaborating MMWH's qualities which can cover pathophysiological constellations being characterized by a combined high risk of thrombosis and bleeding complications.

Thereby emphasis has to be laid upon the spectrum of pharmacological and clinical-therapeutic impact factors directed at the critical dissociation between the anticoagulatory/antithrombotic influences on the one hand and the associated bleeding-potential on the other.

The investigational methods applied are identical to those applied in EP 1 252 194 B1.

To explain the main outcome measures, the clot-score is an integrated measure of the incidence and extent of experimentally induced thrombosis. So, antithrombotic activity expresses itself by the reduction of the clot-score.

The other methodological approach used was based upon the rabbit ear blood loss model whereby the blood loss is assessed by the red blood cells being counted in the saline bath in which the rabbit ear is immersed. The template bleeding time measures the duration of bleeding due to a standardized incision of the rabbit ear, a method worldwide established and refined by J. Fareed (Chicago).

Figure 6:
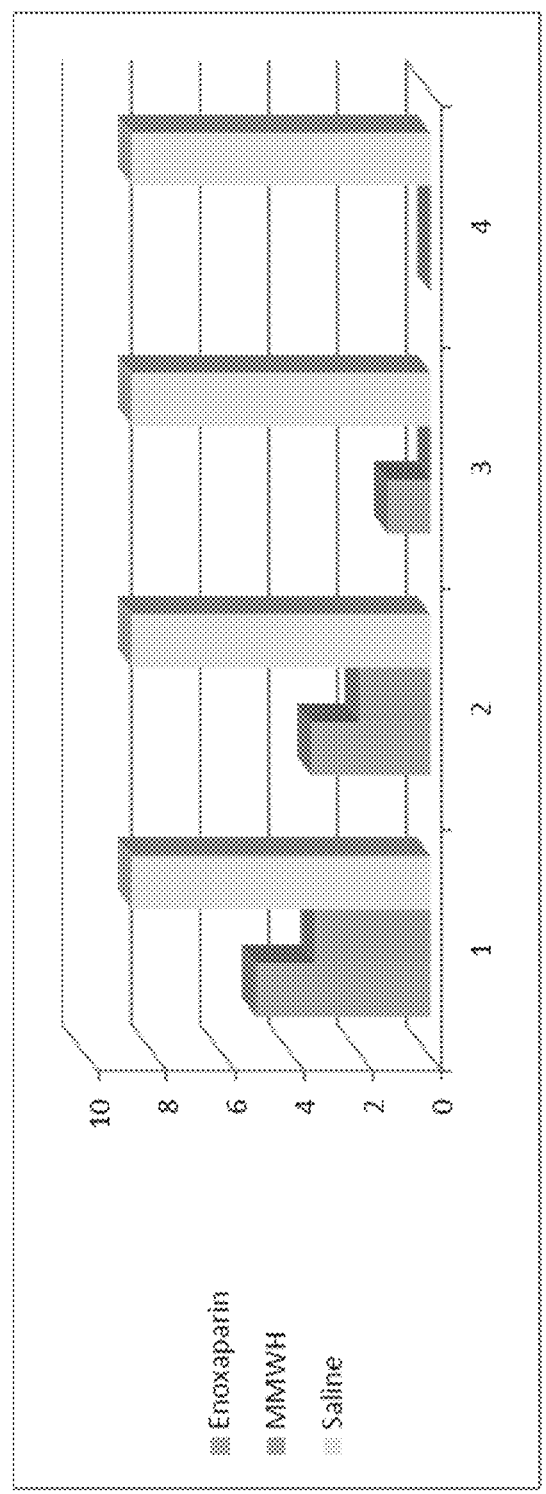
FIG. 6 shows a comparison of the antithrombotic effects of enoxaparin, the MMWH and saline in a modified Wessler thrombosis model by the assessment of the clot score, wherein a reduction of the clot score means reduction of clot formation. The clot score values are also given in Table 2. The numbers 1 to 4 correspond to the rows of Table 2, i.e., the dosages of 5 to 50 U/kg. The bars on the left represent enoxaparin, the bars in the middle represent MMWH and the bars on the right represent saline.
Figure 7:
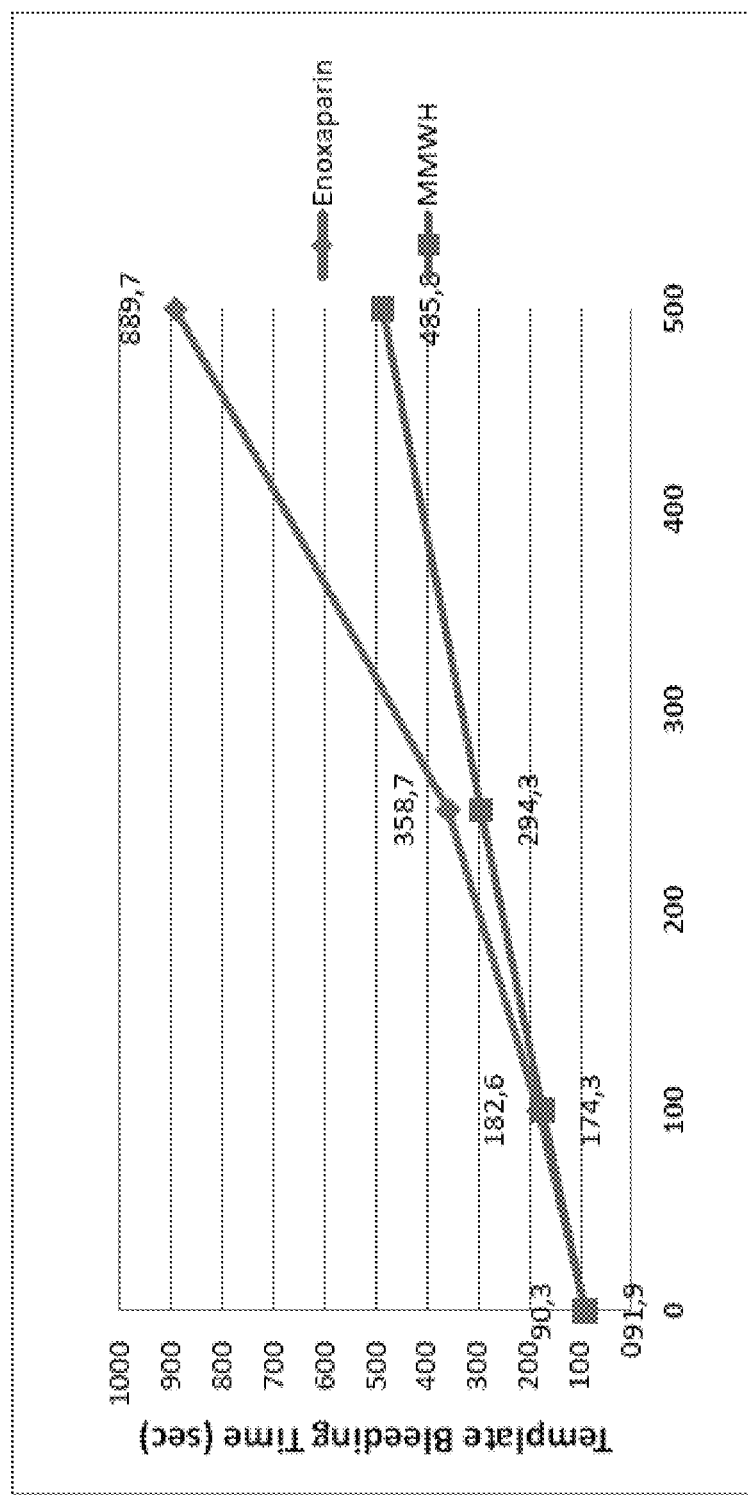
FIG. 7 shows the comparative bleeding effects of enoxaparin and MMWH by means of the template bleeding time after intravenous administration.
Figure 8:
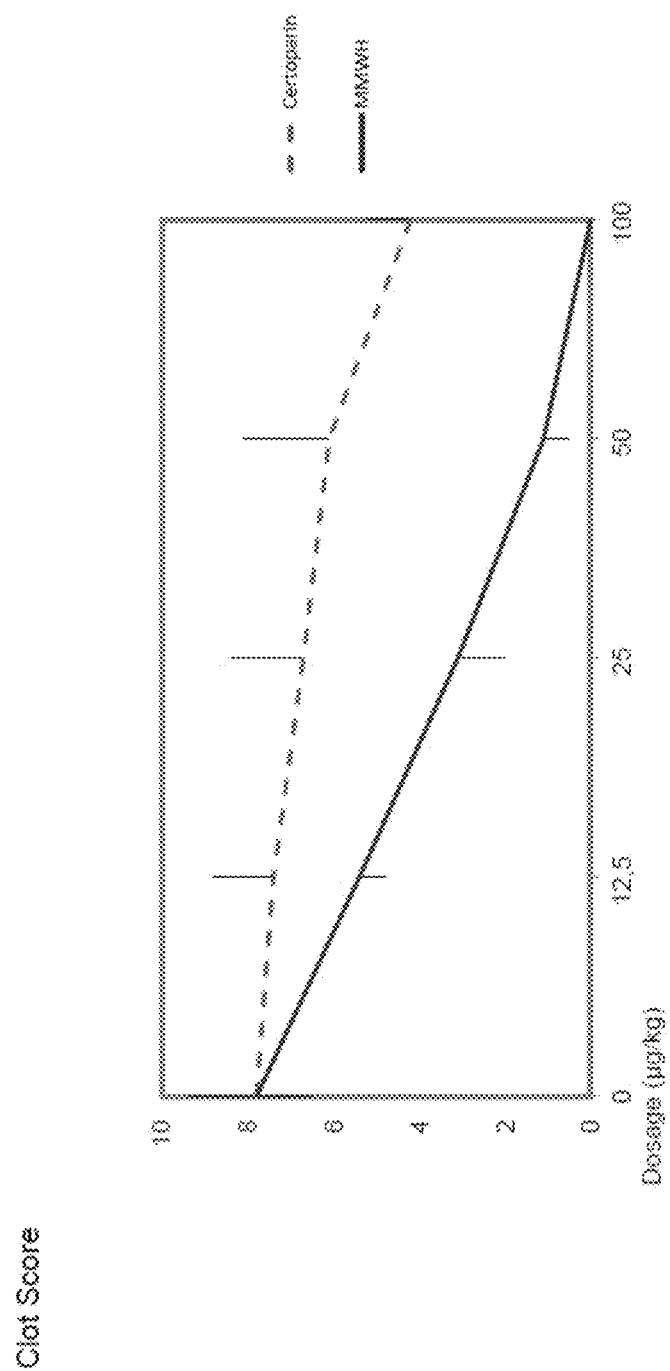
FIG. 8 shows a comparison of the antithrombotic activity of certoparin and MMWH by means of the clot score as a function of the dosage administered intravenously by Fareed et al.

MMWH for use in treatment of venous thromboembolism in malignant disease was compared to two LMWHs, namely enoxaparin and certoparin. The detailed findings laid down in FIGS. 6, 7 and 8 and Tables 2, 3, 4, 5 and 6 furnish consistent evidence of MMWH's surprising superiority over both LMWHs with respect to both antithrombotic efficacy and tolerance.

TABLE 2

Comparative antithrombotic effects of enoxaparin, MMWH and saline in a modified Wessler thrombosis model

|  | Clot Score | | |
|---|---|---|---|
| Doses (U/Kg) | Enoxaparin | MMWH | Saline |
| 5 | 5.1 | 3.41 | 8.7 |
| 10 | 3.5 | 2.13 | 8.7 |
| 25 | 1.25 | 0 | 8.7 |
| 50 | 0 | 0 | 8.7 |

TABLE 3

Antithrombotic actions of the intravenous administration of MMWH and enoxaparin in a rabbit statis thrombosis model. The differences between Enoxaparin and MMWH are statistically significant in favour of the latter and with regard to the doses of 5 U/kg ($p \leq 0.005$) and 25 U/kg ($p \leq 0.001$).

| Rabbit Number | Saline* | 5 U/kg | 10 U/kg | 25 U/kg | 50 U/kg |
|---|---|---|---|---|---|
| a) Antithrombotic effects of intravenous Enoxaparin | | | | | |
| 1 | 8.75 | 5.30 | 2.50 | 2.50 | 0 |
| 2 | 7.50 | 5.00 | 5.00 | 0.00 | 0 |
| 3 | 10.00 | 4.90 | 3.75 | 1.25 | 0 |
| 4 | 10.00 | 5.70 | 3.75 | 1.25 | 0 |
| 5 | 8.75 | 6.00 | 2.50 | 1.25 | 0 |
| 6 | 7.50 | 5.00 | 3.75 | 1.25 | 0 |
| 7 | 8.75 | 5.10 | 2.50 | 2.50 | 0 |
| 8 | 7.50 | 5.20 | 5.00 | 0.00 | 0 |
| 9 | 8.75 | 4.80 | 3.75 | 0.00 | 0 |
| 10 | 10.00 | 3.70 | 2.50 | 2.50 | 0 |
| X ± S.D. | 8.70 ± 1.20 | 5.10 ± 0.58 | 3.50 ± 0.99 | 1.25 ± 1.02 | 0 ± 0 |
| b) Antithrombotic effects of intravenous MMWH | | | | | |
| 1 | 8.75 | 2.70 | 3.75 | 0 | 0 |
| 2 | 7.50 | 3.80 | 1.25 | 0 | 0 |
| 3 | 10.00 | 3.80 | 1.25 | 0 | 0 |
| 4 | 10.00 | 4.00 | 2.50 | 0 | 0 |
| 5 | 8.75 | 3.10 | 2.50 | 0 | 0 |
| 6 | 7.50 | 2.90 | 1.25 | 0 | 0 |
| 7 | 8.75 | 2.70 | 2.50 | 0 | 0 |
| 8 | 7.50 | 2.60 | 2.50 | 0 | 0 |
| 9 | 8.75 | 4.50 | 1.25 | 0 | 0 |
| 10 | 10.00 | 4.00 | 2.50 | 0 | 0 |
| X ± S.D. | 8.70 ± 1.20 | 3.41 ± 0.68 | 2.13 ± 0.84 | 0 ± 0 | 0 ± 0 |

TABLE 4

Antithrombotic actions of the subcutaneous administration of MMWH and enoxaparin in a rabbit statis thrombosis model. The differences between both heparins are significant with regard to the doses of 25 U/kg, 75 U/kg and 100 U/kg ($p < 0.05$-$0.01$).

| Rabbit Number | Saline* | 25 U/kg | 50 U/kg | 75 U/kg | 100 U/kg | 250 U/kg |
|---|---|---|---|---|---|---|
| a) Antithrombotic effects of subcutaneous Enoxaparin | | | | | | |
| 1 | 8.75 | 5.00 | 2.50 | 3.10 | 3.50 | 0 |
| 2 | 7.50 | 5.80 | 5.00 | 2.70 | 1.25 | 0 |
| 3 | 10.00 | 5.30 | 3.75 | 3.60 | 2.50 | 0 |
| 4 | 10.00 | 5.60 | 3.75 | 2.80 | 2.50 | 0 |
| 5 | 8.75 | 5.90 | 3.75 | 2.10 | 2.50 | 0 |
| 6 | 7.50 | 4.90 | 3.75 | 2.90 | 2.50 | 0 |
| 7 | 8.75 | 5.30 | 2.50 | 3.00 | 2.50 | 0 |
| 8 | 7.50 | 5.40 | 5.00 | 2.50 | 1.25 | 0 |
| 9 | 8.75 | 5.50 | 3.75 | 3.75 | 2.50 | 0 |
| 10 | 10.00 | 5.30 | 3.75 | 2.50 | 3.75 | 0 |
| X ± S.D. | 8.70 ± 1.20 | 5.40 ± 0.32 | 3.75 ± 0.83 | 2.90 ± 0.50 | 2.50 ± 0.8.3 | 0 ± 0 |
| b) Antithrombotic effects of subcutaneous MMWH | | | | | | |
| 1 | 8.75 | 4.20 | 2.50 | 2.20 | 0 | 0 |
| 2 | 7.50 | 3.70 | 2.50 | 1.70 | 0 | 0 |
| 3 | 10.00 | 4.10 | 3.75 | 2.10 | 0 | 0 |
| 4 | 10.00 | 4.00 | 2.50 | 2.00 | 0 | 0 |
| 5 | 8.75 | 3.20 | 2.50 | 1.40 | 0 | 0 |
| 6 | 7.50 | 3.90 | 3.75 | 1.30 | 0 | 0 |
| 7 | 8.75 | 4.20 | 2.50 | 1.70 | 0 | 0 |
| 8 | 7.50 | 3.50 | 2.50 | 2.50 | 0 | 0 |
| 9 | 8.75 | 3.50 | 2.50 | 1.50 | 0 | 0 |
| 10 | 10.00 | 4.00 | 3.75 | 2.00 | 0 | 0 |
| X ± S.D. | 8.70 ± 1.20 | 3.83 ± 0.34 | 2.90 ± 0.60 | 1.84 ± 0.38 | 0 ± 0 | 0 ± 0 |

*Based on the I.V. series

TABLE 5

Bleeding due to enoxaparin and MMWH demonstrated in a rabbit ear bleeding model. The test parameter of the template bleeding time is the duration of bleeding (seconds). The differences between both heparins are statistically significant with regard to the doses of 250 U/kg ($p \leq 0.01$) and of 500 U/kg ($p \leq 0.001$).

| Rabbit Number | Saline* [s] | 100 U/kg [s] | 250 U/kg [s] | 500 U/kg [s] |
|---|---|---|---|---|
| a) Bleeding effects of intravenous Enoxaparin (template bleeding time) | | | | |
| 1 | 96 | 170 | 399 | 867 |
| 2 | 86 | 168 | 333 | 999 |
| 3 | 99 | 243 | 367 | 1000 |
| 4 | 60 | 169 | 360 | 828 |
| 5 | 109 | 160 | 323 | 788 |
| 6 | 92 | 188 | 344 | 823 |
| 7 | 88 | 176 | 386 | 806 |
| 8 | 96 | 165 | 348 | 924 |
| 9 | 87 | 191 | 355 | 942 |
| 10 | 90 | 196 | 372 | 920 |
| X ± S.D. | 90.30 ± 12.68 | 182.60 ± 24.38 | 358.70 ± 23.32 | 889.70 ± 78.22 |
| b) Bleeding effects of intravenous MMWH (template bleeding time) | | | | |
| 1 | 96 | 156 | 366 | 388 |
| 2 | 86 | 165 | 289 | 555 |
| 3 | 99 | 230 | 234 | 434 |
| 4 | 60 | 165 | 257 | 589 |
| 5 | 109 | 182 | 367 | 423 |
| 6 | 92 | 167 | 245 | 468 |
| 7 | 90 | 178 | 256 | 488 |
| 8 | 88 | 180 | 299 | 525 |
| 9 | 101 | 158 | 309 | 456 |
| 10 | 98 | 162 | 321 | 532 |
| X ± S.D. | 91.90 ± 13.13 | 174.30 ± 21.57 | 294.30 ± 47.53 | 485.80 ± 63.69 |

TABLE 6

Assessment of bleeding due to MMWH and enoxaparin in a rabbit ear blood loss model. The differences between both heparins in favour of MMWH are significant with regard to those doses the effects of which are different from baseline i.e. 250 U/kg ($P \leq 0.05$) and of 500 U/kg ($P \leq 0.001$). The test parameter controlled is RBC as based on the total number of red blood cells in the immersion fluid (see procedure published in EP 1 252 194 B1).

| Rabbit Number | Saline* RBC × $10^9$/L | 25 U/kg RBC × $10^9$/L | 50 U/kg RBC × $10^9$/L | 100 U/kg RBC × $10^9$/L | 250 U/kg RBC × $10^9$/L | 500 U/kg RBC × $10^9$/L |
|---|---|---|---|---|---|---|
| a) Bleeding effects of intravenous Enoxaparin | | | | | | |
| 1 | 0.08 | 0.13 | 0.14 | 0.10 | 0.28 | 0.44 |
| 2 | 0.09 | 0.09 | 0.12 | 0.09 | 0.25 | 0.46 |
| 3 | 0.06 | 0.10 | 0.12 | 0.14 | 0.26 | 0.36 |
| 4 | 0.10 | 0.12 | 0.14 | 0.12 | 0.23 | 0.28 |
| 5 | 0.12 | 0.08 | 0.10 | 0.12 | 0.22 | 0.28 |
| 6 | 0.09 | 0.14 | 0.10 | 0.10 | 0.29 | 0.33 |
| 7 | 0.10 | 0.13 | 0.12 | 0.14 | 0.21 | 0.38 |
| 8 | 0.10 | 0.12 | 0.13 | 0.13 | 0.27 | 0.40 |
| 9 | 0.11 | 0.11 | 0.14 | 0.15 | 0.25 | 0.42 |
| 10 | 0.10 | 0.10 | 0.13 | 0.13 | 0.24 | 0.32 |
| X ± S.D. | 0.10 ± 0.02 | 0.11 ± 0.02 | 0.12 ± 0.01 | 0.12 ± 0.02 | 0.25 ± 0.03 | 0.37 ± 0.06 |
| b) Bleeding effects of intravenous MMWH. | | | | | | |
| 1 | 0.08 | 0.06 | 0.13 | 0.13 | 0.17 | 0.25 |
| 2 | 0.09 | 0.10 | 0.10 | 0.14 | 0.19 | 0.22 |
| 3 | 0.12 | 0.10 | 0.10 | 0.11 | 0.20 | 0.26 |
| 4 | 0.10 | 0.13 | 0.15 | 0.15 | 0.18 | 0.23 |
| 5 | 0.13 | 0.14 | 0.14 | 0.10 | 0.15 | 0.21 |
| 6 | 0.12 | 0.14 | 0.16 | 0.11 | 0.10 | 0.24 |
| 7 | 0.08 | 0.14 | 0.14 | 0.14 | 0.11 | 0.27 |
| 8 | 0.10 | 0.10 | 0.15 | 0.16 | 0.12 | 0.29 |
| 9 | 0.10 | 0.08 | 0.13 | 0.18 | 0.14 | 0.28 |
| 10 | 0.10 | 0.12 | 0.15 | 0.18 | 0.18 | 0.25 |
| X ± S.D. | 0.10 ± 0.02 | 0.11 ± 0.03 | 0.14 ± 0.02 | 0.15 ± 0.03 | 0.17 ± 0.4 | 0.25 ± 0.03 |

The experimental setting for the proof of MMWH's antithrombotic activity resembles the pathophysiological pattern of advancing symptomatic thrombosis as typical for malignancies. As a matter of fact, the experiments fall in the range of manifest thrombogenesis reflected by fill-grown thrombosis that go beyond the stage of mere hypercoagubility, in which the generation of thrombin and its decay are still in balance.

In essence the results in terms of effectiveness and tolerance give verifiable reasons for the heightened benefit-risk ratio of MMWH with respect to LMWH which paves the way to an improved management of VTE In malignant disease. The detachment of MMWH's antithrombotic action from its influence upon bleeding, i.e., the differential impact upon the outcome measures as compared to enoxaparin (see FIG. 6 vs FIG. 7) is of fundamental significance.

The conclusion is downright. In respect to the weaker anticoagulatory/antithrombotic efficacy of enoxaparin the enhanced bleeding-intensity associated can only be due to non-anticoagulatory, nevertheless bleeding-inducing molecules.

As a matter of fact MMWH's surprisingly extraordinary superior tolerance is obviously based on the exclusion of such type harmful molecules with the effect that bleeding is curtailed despite of the increased anticoagulatory/antithrombotic impact.

The doubly Improved benefit-risk ratio attributable to MMWH, i.e., the combination of heightened antithrombotic efficacy with reduced bleeding intensity offers a surprising and unprecedented access to personalized medicine in the management of VTE in malignant disease. The improved benefit-risk ratio permits some differentiated dosage-regimen according to whether the risk of VTE or bleeding is considered the dominant one.

The generally accepted principle in the development of antithrombotic drugs stipulates that the standards of efficacy and tolerance as established for the benchmark LMWH enoxaparin have to be observed meticulously.

So a special biometrical procedure in comparing both heparins was undertaken: The antithrombotic efficacy of MMWH and enoxaparin were defined in terms of the equitolerable doses and the bleeding effects in terms of the equi-effective (antithrombotic) ones.

Accordingly, regression curves according to Prof. Fareed's reported as related to the clot-score, bleeding time, and blood loss were established leading to:
 1. Equi-effective doses according to the clot-score model:
  MMWH dose=0.56 enoxaparin dose
 2. Equitolerable doses according to the blood-loss model:
  MMWH dose=1.78 enoxaparin dose,
  and according to the bleeding time model:
  MMWH dose=1.58 enoxaparin dose In accordance with this analysis the therapeutic dose of MMWH could be increased by 58 to 78% or decreased by 44% in comparison with enoxaparin without cuts in tolerance or efficacy respectively as against the benchmark heparin.

Thus, MMWH is equipped with a unique pharmacodynamic reserve to be mobilized for the benefit of special target-populations. e.g., for patients with anticipated problems of bleeding or with an excessive risk of thrombosis according to the Caprini-score. In the end the modern trend to personalized medicine in malignancies will be extended to the field of antithrombotic prophylaxis and therapy.

As has been mentioned above, fibrin restricts the anticoagulatory action of unfractionated heparin (UFH) known from the prior art. MMWH, however, due to its sharp-cut molecular profile (FIG. 1). i.e., by the exclusion of long-chain molecules, is not subject to this type of limitation of its anticoagulant action. As has been found by P. J. Hoog et al. (J. of Biological Chemistry 1990, 265, 241-246), heparin species of molecular weight less than 11.2 kD are much less effective in promoting thrombin-binding to fibrin than the high-molecular weight ones.

Figure 9:
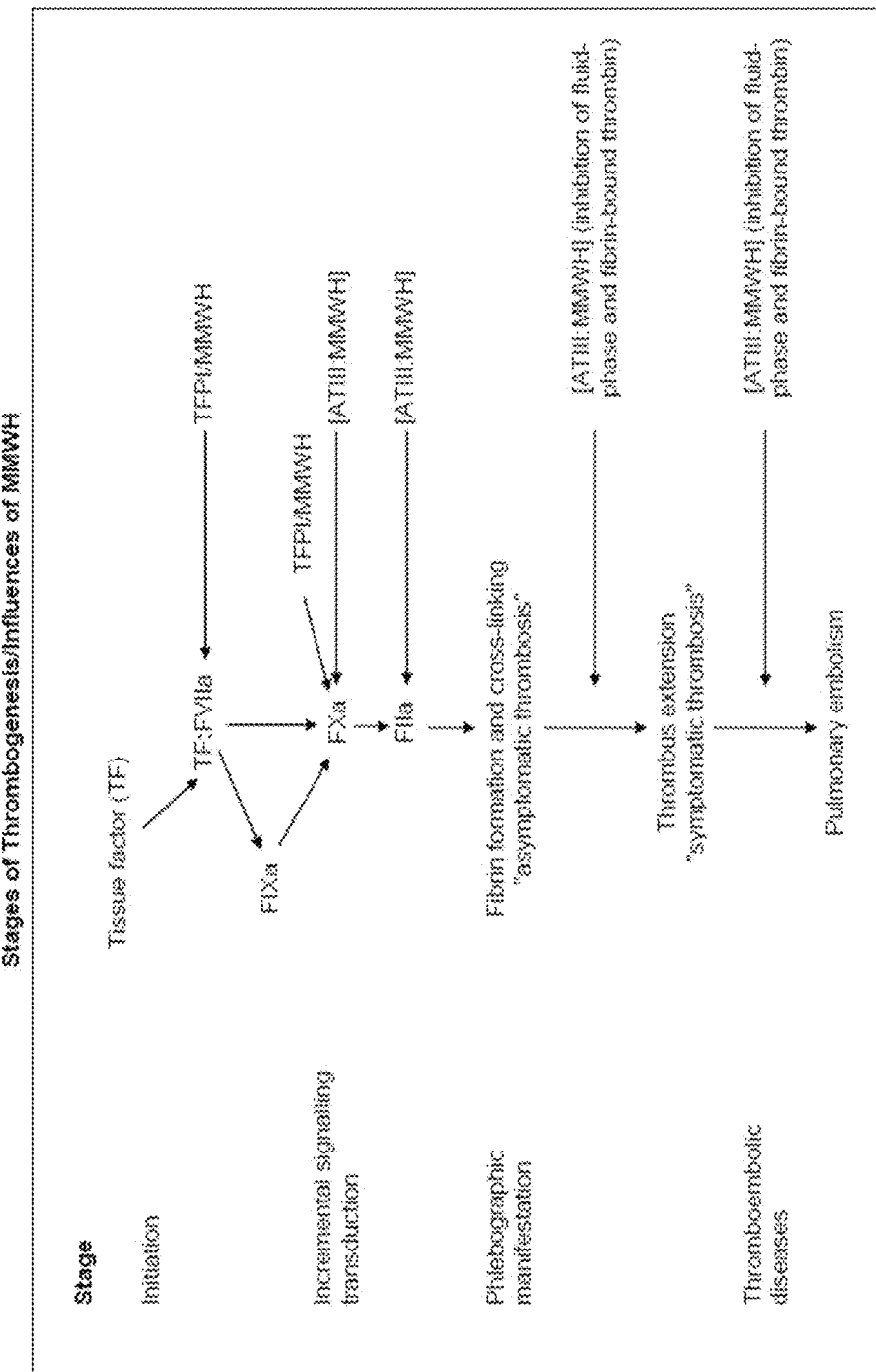
FIG. 9 depicts a schematic overview of the influences of MMWH on the stages of thrombogenesis.

MMWH lends itself for overcoming the therapeutic dilemma of advancing, symptomatic thrombosis (FIG. 9): On the one hand its molecular profile does not promote thrombin-binding to fibrin, on the other its anti-thrombin-activity is high enough, as a matter of fact the highest among heparins. (FIG. 1). MMWH's pharmacodynamic potential in symptomatic VTE not least makes up its specific appropriativeness in malignant disease.

Figure 10:
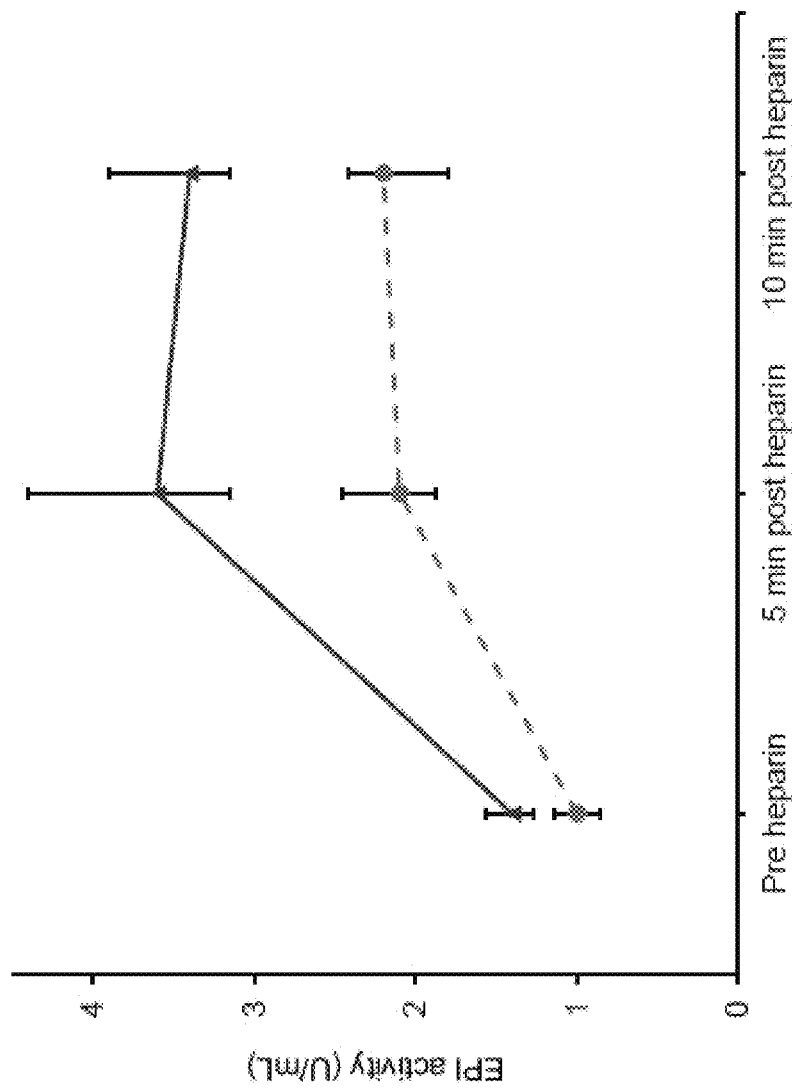
FIG. 10 shows a comparison of the TFPI activity response to heparin in cancer patients and a control group before and after injection of 3000 U heparin by A. K. Lindahl et al. (Thrombosis Research 1999, 59, p. 651-565).

As mentioned above, the tissue factor pathway inhibitor (TFPI) contributes significantly (about one third) to the anticoagulatory potential of heparin. The contributory share of TFPI appears all the more important, because its heparin-dependent release in malignancies is specifically augmented. (FIG. 10) So an accentuated antithrombotic synergism can be anticipated based upon the recruitment of that complementary defense-mechanism by MMWH.

Figure 11:
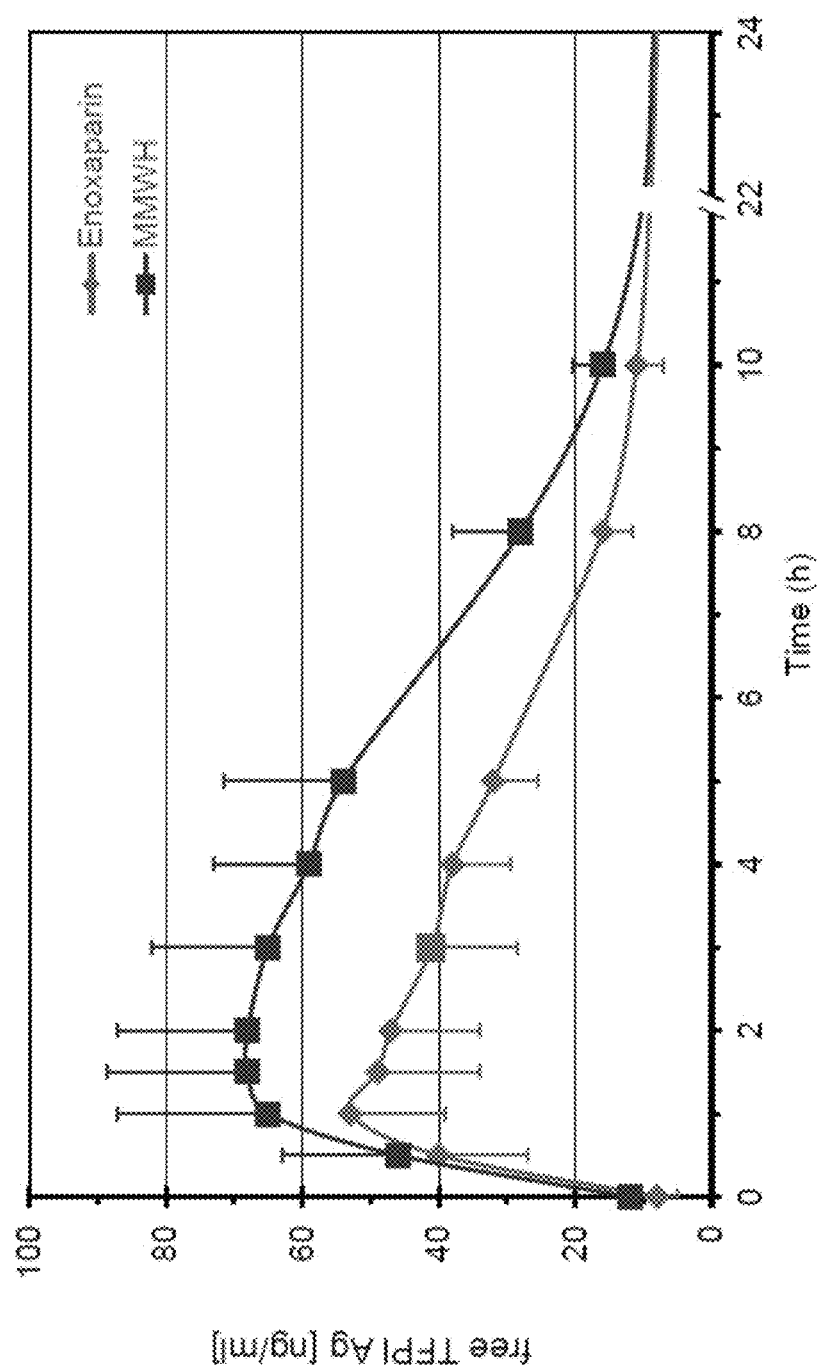
FIG. 11 shows the time evolution of the concentration of carrier-free TFPI after subcutaneous application of the MMWH with an average molecular mass of 10.5 kD, UFH and enoxaparin, 9000 U each. 9000 U correspond to 52 mg MMWH and 90 mg enoxaparin. Results of randomized, double-blind, cross-over study S. Alban (Kiel).

An experimental-clinical investigation is given prominence. That is a randomized, double-blind, multiple cross-over trial on 16 healthy male subjects with the results demonstrated being unique. MMWH brings about a 2 times higher concentration of carrier-free TFPI (AUC O-24 h) as compared to enoxaparin with the gravimetric-based dose of the latter being 1.7 times higher (FIG. 11). Such a differentiation between various heparin was never reported before.

Figure 12:
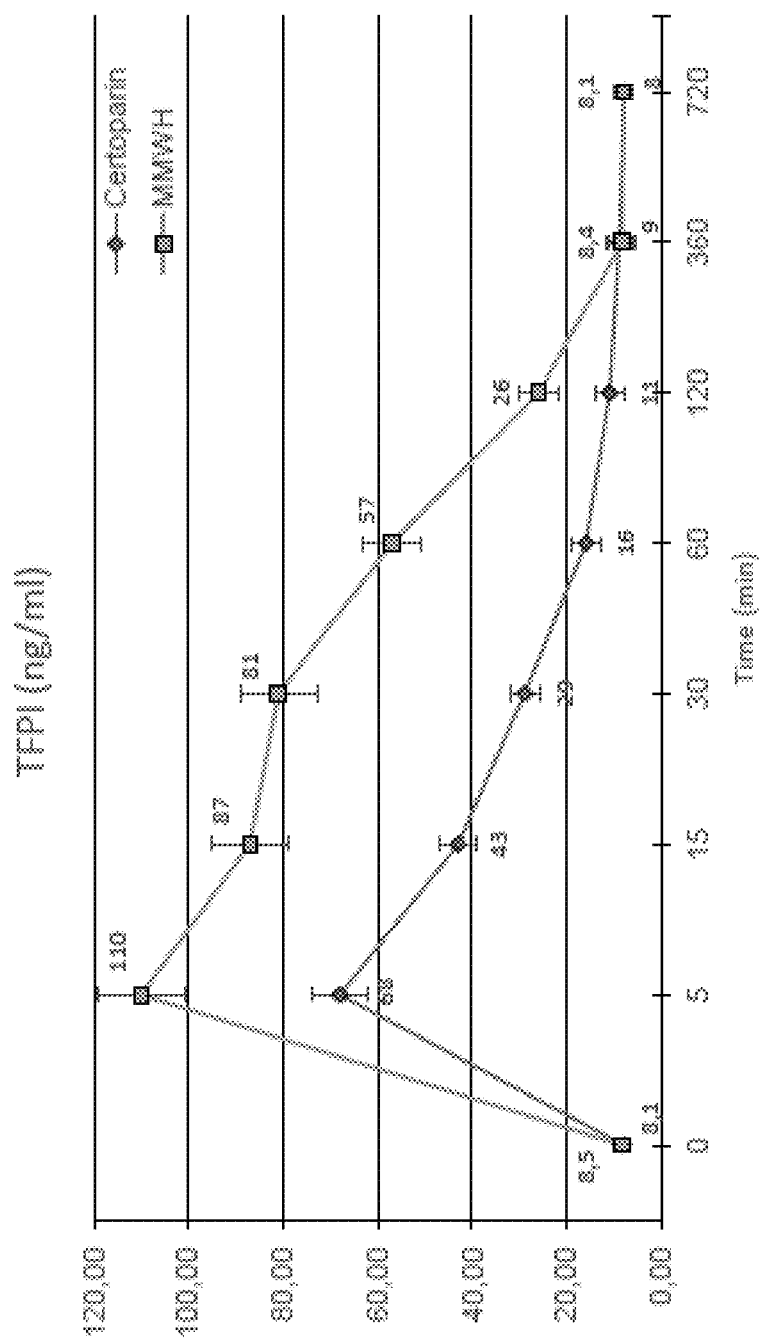
FIG. 12 shows a comparison of the TFPI release by the inventive MMWH and certoparin after intravenous administration of a 1 mg/kg dose. The TFPI values are also given in Table 7.

In order to corroborate the TFPI-related rationale an additional animal-experimental comparison was carried out with the LMWH certoparin (MW 4.2 to 6.2 kD), the gravimetrical-based dose applied being 1 mg/kg (FIG. 12, Table 7) That is a dose-regimen corresponding to that of enoxaparin and certoparin in the treatment of VTE

TABLE 7

Comparative study of the TFPI-release by MMWH and certoparin TFPI (Ng/ml)

| Time (min) | Certoparin | MMWH |
| --- | --- | --- |
| 0 | 8.1 ± 1.3 | 8.5 ± 1.3 |
| 5 | 68 ± 6 | 110 ± 9 |
| 15 | 43 ± 4 | 87 ± 8 |
| 30 | 29 ± 3 | 81 ± 8 |
| 60 | 16 ± 3 | 57 ± 6 |
| 120 | 11 ± 3 | 26 ± 4 |
| 360 | 9 ± 3 | 8.4 ± 3 |
| 720 | 8 ± 2 | 8.1 ± 2 |

The surprising superiority of MMWH over LMWH can only be classified as exceptional. In this respect a comparative trial on UFH and gammaparin (MW 4.7 to 5.7 kD) carried out by M. Quim et al. (Thromb Res 2007, 119, p. 653-61) may be worth mentioning with no significant differences in terms of TFPI release between the two agents being noted.

Figure 13:
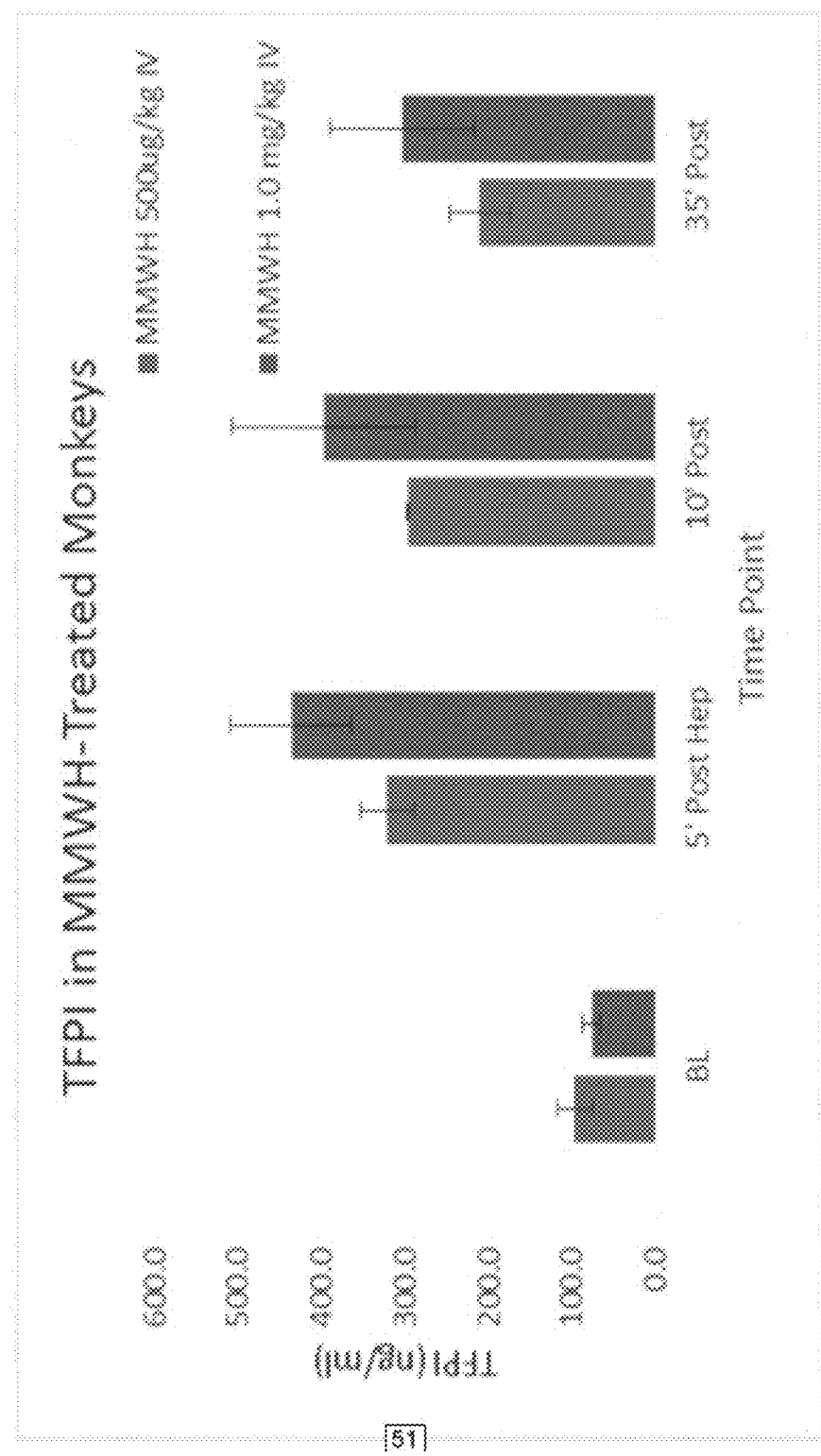
FIG. 13 shows a comparison of the TFPI concentration response to different doses of MMWH in monkeys. The bars on the left represent a dosage of 500 µg/kg and the bars on the right represent a dosage of 1.0 mg/kg.

To round off the pertinent documentation of MMWH, its impact on TFPI-release in primates was studied which connotes the dose-dependent pharmacokinetics in men (FIG. 13). It can be concluded that the inventive MMWH is particularly suited for the management of VTE in malignant disease.

All the more one has got to look for plausible reasons for the observed dissociation between MMWH's effectiveness and the inherent tendency towards bleeding, as demonstrated above. If antithrombotic activity and tolerance (absence of bleeding complications) were just inversely and invariably associated, then it were not conceivable that the former could be intensified without making allowances for the latter. Such association, however, is not a regular one.

The central rationale of MMWH's narrow molecular spectrum involves the complete exclusion of the low molecular weight faction, i.e., the vast amounts of LAM associated. What gives this investigation expressive meaning is that the ratio of HAM/LAM in the experimental heparin species compared to UFH exactly corresponds to that of enoxaparin. Of no less importance than the reduction of LAM appears the exclusion of the long-chain fraction (MW greater than 12 kD) of heparin because it also exerts prohaemorrhagic effects.

These are the detailed and plausible reasons for MMWH's sharp-cut molecular profile with the benefit of an unparalleled anticoagulatory activity, unballasted by detrimental molecules.

In essence some meaningful additional explanation is offered for the heightened benefit-risk ratio of MMWH which essentially originates in the double-pronged exclusion of prohemorrhagic molecular species from MMWH's molecular spectrum.

MMWH, in sharp contrast to LMWH, lends itself to APTT-control if found necessary in order to ensure safety and effectiveness in complex hemostaseological settings, e.g., in intensive care and advanced malignancies with disturbances of the coagulation system.

As a matter of fact, beyond its function in critical cases, the APTT can even serve to potentiate the basic antithrombotic effectiveness of MMWH, a possibility principally closed to LMWH.

So the APTT appears a laboratory instrument to complement the genuine qualities of MMWH in malignancies thus once more supporting its exceptional positioning among heparins.

And last but not least there is another difference in relation to LMWH. MMWH can be fully and instantaneously neutralized with protamin which appears of major importance in life-threatening bleeding complications in malignant disease, and such a procedure requires APTT-control.

A preferred embodiment of the present invention is a MMWH for use in the treatment of venous thromboembolism in cancer, particularly cancer complicated by renal disease.

Figure 14:
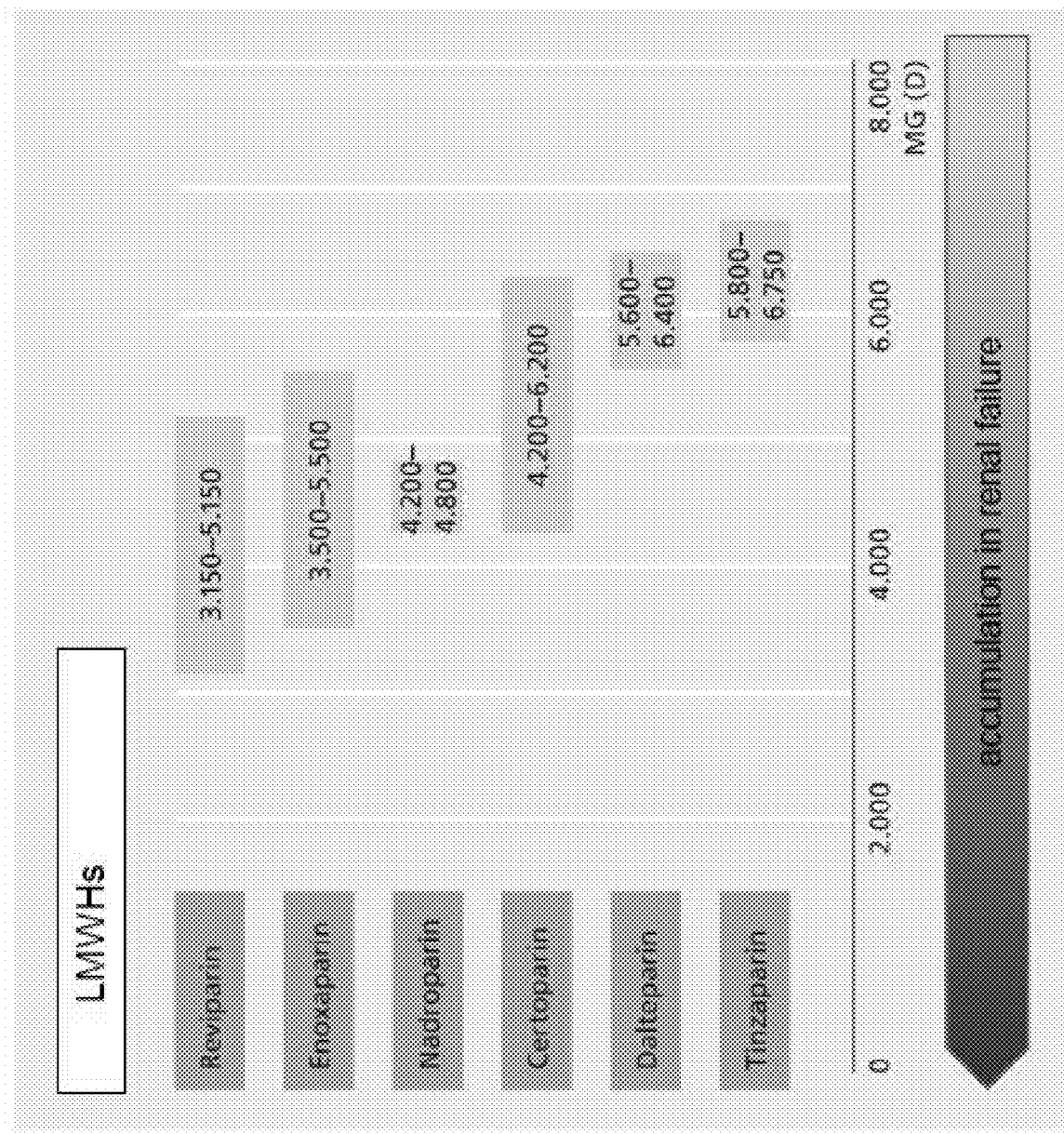
FIG. 14 depicts the risk of renal failure of LMWHs as a function of their molecular weight by H. Schinzel (Vascular Care 2007, 12, 18-28).
Figure 15:
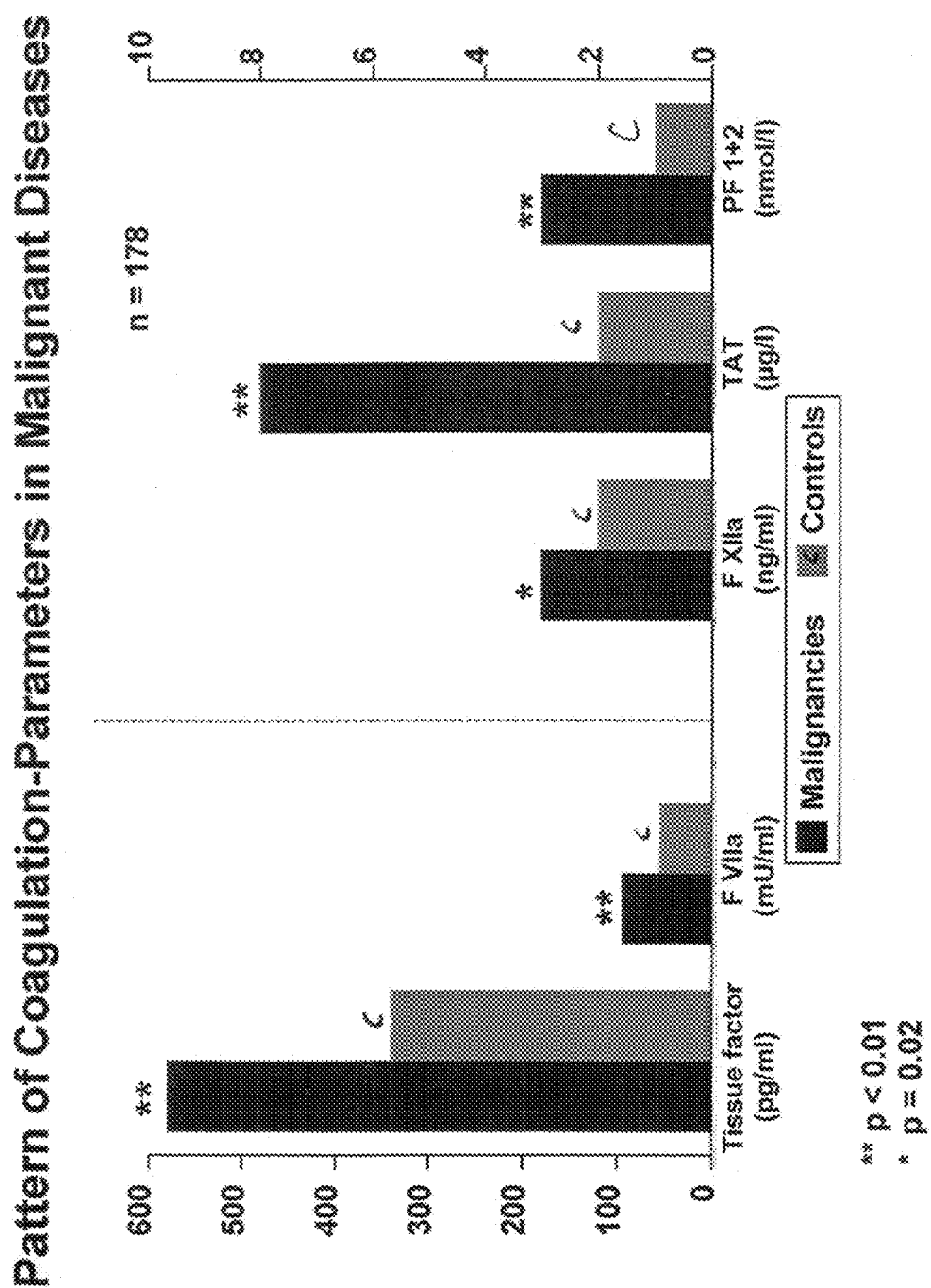
FIG. 15 shows the pattern of coagulation-parameters in malignant disease as investigated by A. K. Kakkar et al. (Lancet 1995, 346, 1004-5).
Figure 16:
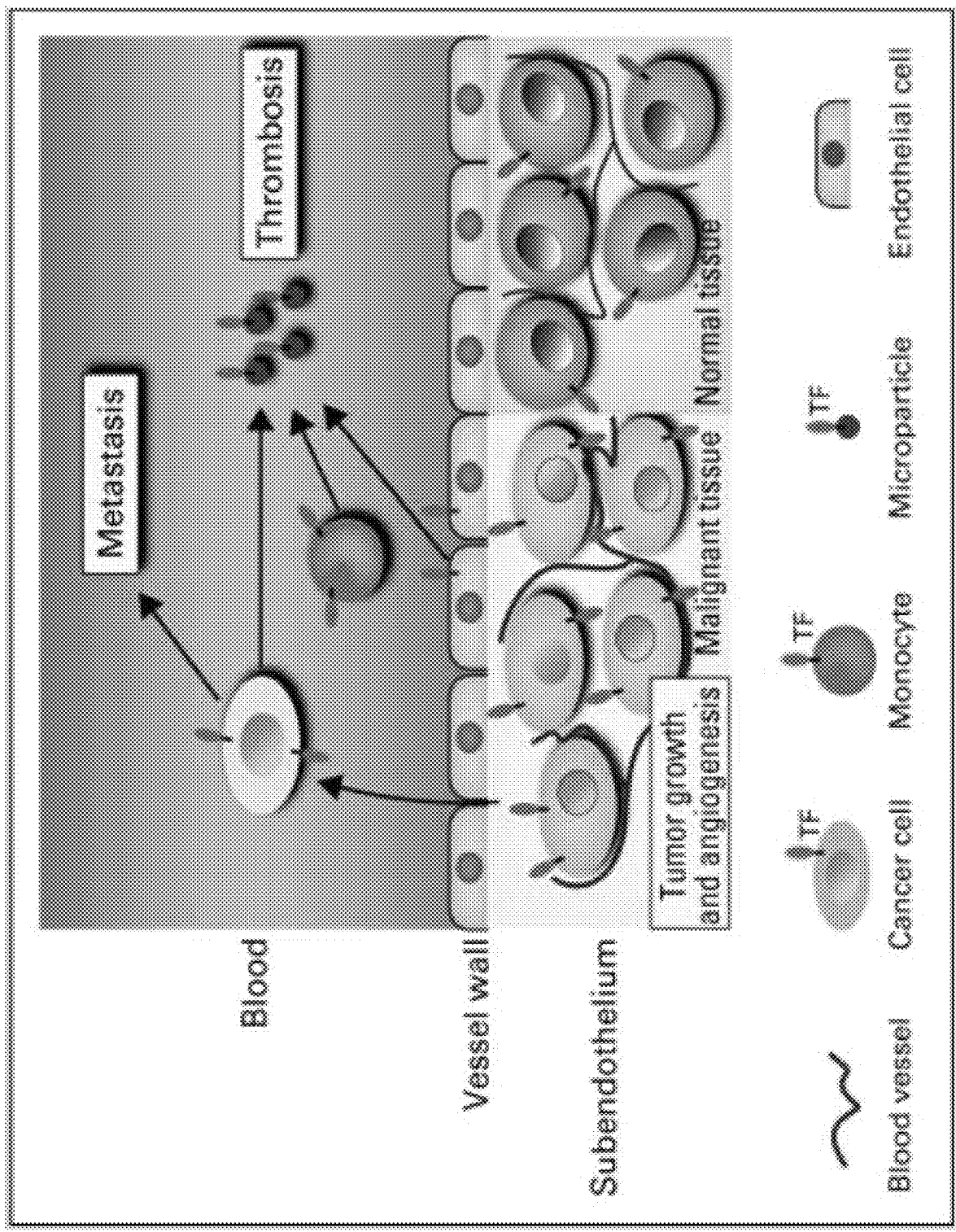
FIG. 16 shows how, according to R. S. Kastkuri et al. (J. Clin. Oncol. 2009, 27, 4834-4838), tissue factor (TF) contributes to tumor growth and thrombosis in patients with cancer and the release of TF-positive microparticles by tumor cells, blood cells, and endothelium cells into blood triggers VTE.
Figure 17:
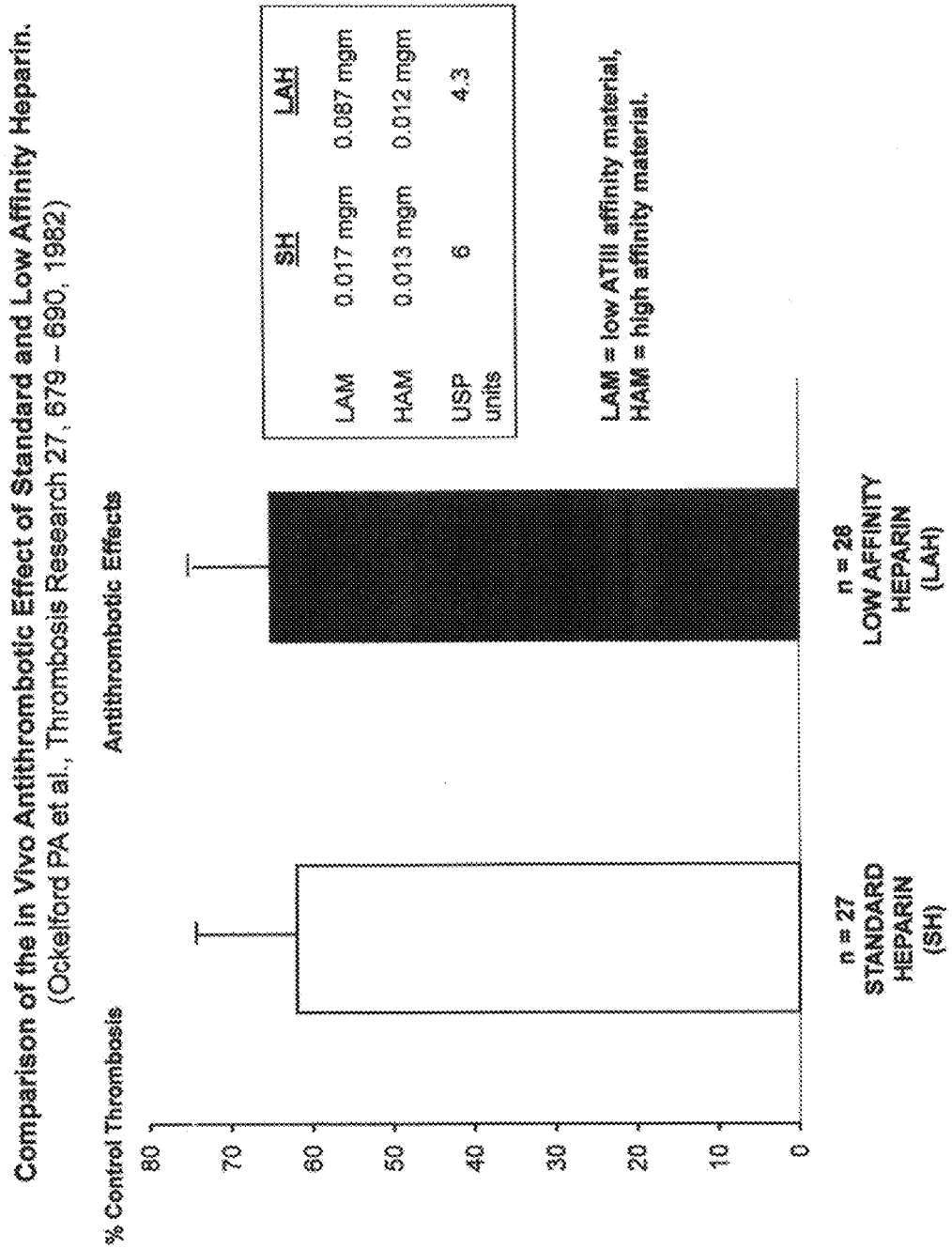
FIG. 17 shows a comparison of the in vivo antithrombotic effect of standard and low affinity heparin by P. A. Ockelford et al. (Thrombosis Research 1982, 27, 679-690).

The preferred MMWH for in use in treatment of cancer complicated by renal disease is under favourable auspices: MMWH is not subject to bio-accumulation. The reason for that pharmacokinetic advantage, as shared with UFH, originates from the fact that heparins with some larger molecules are mostly eliminated from the body by extrarenal mechanisms which do not imply a significant risk of bio-accumulation in blood (FIG. 14).

The frequent combination of an enhanced risk of VTE and haemorrhage favours its use in renal failure of whatever pathogenesis. As a matter of fact there are no caveats or contraindications looming up in severe renal impairment as in case of LMWHs, and that no dose-reductions would have to be considered. Surprisingly, MMWH is even superior to dalteparin and tinzaparin because it is completely devoid of short heparin-chains readily accumulating.

The invention claimed is:
1. A process for the treatment of venous thromboembolism in cancer complicated by renal disease, comprising:
   administering an effective amount of a medium molecular weight heparin to a subject for the treatment of venous thromboembolism in cancer complicated by renal disease, wherein the medium molecular weight heparin has an average molecular weight of more than 9 kD and less than 12 kD.

* * * * *